(12) United States Patent
Osterloh et al.

(10) Patent No.: US 11,235,169 B1
(45) Date of Patent: Feb. 1, 2022

(54) ILLUMINATION DEVICE FOR PHOTODYNAMIC THERAPY, METHOD FOR TREATING A SKIN DISEASE AND METHOD FOR OPERATING AN ILLUMINATION DEVICE

(71) Applicant: BIOFRONTERA PHARMA GMBH, Leverkusen (DE)

(72) Inventors: Markus Osterloh, Leverkusen (DE); Ben Novak, Leverkusen (DE); Hermann Lübbert, Leverkusen (DE)

(73) Assignee: BIOFRONTERA PHARMA GMBH, Leverkusen (DE)

( * ) Notice: Subject to any disclaimer, the term of this patent is extended or adjusted under 35 U.S.C. 154(b) by 0 days.

(21) Appl. No.: 17/215,785

(22) Filed: Mar. 29, 2021

Related U.S. Application Data

(63) Continuation-in-part of application No. 17/071,496, filed on Oct. 15, 2020.

(51) Int. Cl.
  *A61N 5/06* (2006.01)
  *A61K 41/00* (2020.01)

(52) U.S. Cl.
  CPC .......... *A61N 5/062* (2013.01); *A61K 41/0057* (2013.01); *A61N 5/0616* (2013.01); *A61N 2005/0633* (2013.01)

(58) Field of Classification Search
  CPC ...... A61N 5/06; A61N 5/0613; A61N 5/0616; A61N 5/062; A61N 2005/0626;
  (Continued)

(56) References Cited

U.S. PATENT DOCUMENTS 5,269,778 A 12/1993 Rink et al.
6,223,071 B1 * 4/2001 Lundahl ................. A61N 5/062
  600/476

(Continued)

FOREIGN PATENT DOCUMENTS

WO  WO 2011/038923 A2  4/2011
WO  WO 2015/028541 A1  3/2015

OTHER PUBLICATIONS

U.S. Appl. No. 17/056,170, filed Jun. 5, 2019.
(Continued)

Primary Examiner — Ahmed M Farah
(74) Attorney, Agent, or Firm — Leydig, Voit & Mayer, Ltd.

(57) ABSTRACT

An Illumination device (100) for photodynamic therapy is provided, the illumination device comprising at least one electromagnetic radiation emitting unit (10), the at least one electromagnetic radiation emitting unit comprising at least one electromagnetic radiation source (1), the electromagnetic radiation source being configured to generate radiation for the irradiation of a region of an irradiation object in an illumination session, wherein the irradiation object is to be arranged at a predetermined object location (300), wherein the predetermined object location is arranged at a distance relative to a radiation output area (11) of the radiation emitting unit through which the radiation generated by the at least one electromagnetic radiation source exits the radiation emitting unit during operation of the illumination device (100).

20 Claims, 9 Drawing Sheets

(58) Field of Classification Search
CPC .... A61N 2005/0627; A61N 2005/0628; A61N 2005/0629; A61N 2005/0633; A61N 2005/0642; A61N 2005/0643; A61N 2005/065; A61N 2005/0651; A61N 2005/0652; A61N 2005/0662; A61K 41/0057; A61K 41/0061
USPC .................. 607/88–91, 96, 100; 128/898
See application file for complete search history.

(56) References Cited

U.S. PATENT DOCUMENTS

| | | | |
|---|---|---|---|
| 6,709,446 B2* | 3/2004 | Lundahl | A61N 5/062 607/88 |
| 2005/0024853 A1 | 2/2005 | Thomas-Benedict | |
| 2005/0075703 A1* | 4/2005 | Larsen | A61N 5/062 607/88 |
| 2006/0253175 A1* | 11/2006 | Fan | A61N 5/062 607/88 |
| 2013/0304019 A1* | 11/2013 | Cooper | A61N 5/062 604/501 |
| 2014/0067024 A1* | 3/2014 | Jones | A61N 5/0616 607/90 |
| 2014/0207211 A1 | 7/2014 | Lee et al. | |
| 2017/0216616 A1* | 8/2017 | Boyajian | A61N 5/062 |

OTHER PUBLICATIONS

U.S. Appl. No. 17/071,496, filed Oct. 20, 2020.
U.S. Appl. No. 17/071,496, filed Oct. 15, 2020.
International Search Report and Written Opinion, dated Feb. 28, 2020, corresponding to International Application No. PCT/EP2019/064642 (filed Jun. 5, 2019), 16 pp.

* cited by examiner

ILLUMINATION DEVICE FOR PHOTODYNAMIC THERAPY, METHOD FOR TREATING A SKIN DISEASE AND METHOD FOR OPERATING AN ILLUMINATION DEVICE

CROSS REFERENCE TO RELATED APPLICATIONS

This application is a continuation-in-part application of U.S. application Ser. No. 17/071,496, filed Oct. 15, 2020, which is incorporated herein in its entirety.

FIELD OF THE INVENTION

This disclosure relates to an illumination device for photodynamic therapy and a method for treating a skin disease. Furthermore, the disclosure relates to a method for operating an illumination device and a computer program product as well as a computer-readable medium.

BACKGROUND

Photodynamic therapy (PDT) has been widely studied and several approaches have been used successfully for treatment. In general, there are three requirements for PDT: a photosensitizer, molecular oxygen and light of a specific wavelength. For dermatological PDT usually a prodrug, for example aminolevulinic acid (ALA), is topically applied to the skin. Subsequently, the prodrug is then converted by the cells, e.g. by neoplastic cells, into the actual photosensitizer. The molecular mechanism of action in PDT is based on cellular ALA uptake, synthesis and accumulation of the photosensitizer, which can be excited by light of specific wavelengths leading to the formation of reactive oxygen species (ROS), upon the presence of oxygen. The ROS can initiate cell death, e.g. in the form of apoptosis, necrosis and autophagy.

However, one of the major issues that hinder broad acceptance of PDT by patients is the relatively high amount of pain perceived by the patients during the illumination which ranges from mild inconvenience to severe pain to a point where the treatment has to be aborted. In addition, although PDT is a highly effective treatment method, reoccurrence of some diseases like actinic keratosis is common and thus patients often, although having been successfully treated, later develop different lesions at different skin areas and again require medical intervention. Moreover, some patients are not completely cured after a single PDT session and require a second session. If the first PDT they received was very painful the chances of beginning or completing a second PDT are small despite the fact that it offers supreme efficacy compared to other therapy options. As a result, the acceptance of many patients to undergo treatment or re-treatment decreases. This of course has great negative implications for an individual PDT and PDT as a whole.

Nevertheless, PDT efficacy is also limited by any of the involved factors, i.e. photosensitizer, oxygen, and light. Reduced availability of any of these factors may hamper with ROS formation. Optimized pharmaceutical forms, pre-treatments and incubation modalities can ensure proper and abundant deposition of the photosensitizer. Still, light has to reach a molecule in sufficient quantities and oxygen needs to be present as an energy acceptor.

In particular the light of the illumination at the appropriate wavelength to activate the respective photosensitizer needs to be made available at a sufficient dose. For topical applications, a frequently used photosensitizer is protoporphyrin IX (PpIX), mostly produced in skin cells by application of a precursor molecule, such as ALA. PpIX can be activated by light of a variety of different wavelengths of which red (approx. 635 nm), blue (approx. 420 nm), yellow (approx. 542 nm) or green (approx. 506 nm) light are most frequently used. Generally, a light dose received by a target, e.g. the treated skin, depends on three main factors. The irradiance provided by the illumination device, the distance between the target area and the illumination device, and the duration of the illumination.

The current practice is to apply the entire light dose within a short interval (for example ranging from 7 to 12 minutes with red light or 15-20 minutes with blue light). Usually, this approach is limited by the occurrence of pain. Moreover, photobleaching of the photosensitizer may occur to a greater extent at higher light intensities and may limit the treatment efficiency. Photobleaching describes the effect that the photosensitizer is inactivated by permanent disruption of its chemical structure, e.g. by cleavage of covalent bonds. This photobleaching effect may coincide with temporal oxygen depletion in the target tissue due to a massive initial reaction. This leads to a rapid decrease in oxygen, which is required for ROS formation. All photobleaching that occurs during the phase where oxygen is limited is likely to be unproductive, as it yields fewer cytotoxic singlet oxygen.

It should be noted that the statements above should not be construed as being admitted prior art. They are only made to illustrate the background of the presently disclosed concepts and may not have been made available to the public yet.

SUMMARY OF THE INVENTION

One object to be achieved is to provide an improved illumination device for photodynamic therapy. A further object to be achieved is to provide a method for treating a skin disease in which such an illumination device is used. A further object to be achieved is to provide a method for operating such an illumination device.

The respective object may, inter alia, be achieved by the subject matter of claims 1, 17 and 18. Advantageous embodiments and further developments are the subject of the dependent claims. However, further advantageous concepts may be disclosed herein besides the ones which are currently claimed.

Firstly, the illumination device is specified in more detail.

According to at least one embodiment, the illumination device comprises at least one electromagnetic radiation emitting unit. "At least one" means that the illumination device may comprise one or more radiation emitting units. All features which are in the following disclosed for one radiation emitting unit are likewise disclosed for all other radiation emitting units of the illumination device or only for some radiation emitting units of the device. The radiation emitted by the radiation emitting unit is, for example, radiation in the visible wavelength region.

According to at least one embodiment, the electromagnetic radiation emitting unit comprises at least one electromagnetic radiation source. This means, that the electromagnetic radiation emitting unit may comprise one or more electromagnetic radiation sources, particularly several radiation sources. All features which are in the following disclosed for one electromagnetic radiation source are likewise disclosed for all electromagnetic radiation sources of the radiation emitting unit or of the illumination device or only some radiation sources.

According to at least one embodiment, the electromagnetic radiation source is configured to generate radiation for the irradiation of a region of an irradiation object in an illumination session. Thus, the electromagnetic radiation source is an element of the electromagnetic radiation emitting unit which produce the radiation emitted by the radiation emitting unit. The irradiation object is, for example, a mammal, e.g. a human. The region of the irradiation object to be irradiated is, for example, a skin region of the human. An illumination session lasts, for example, at most 30 min.

According to at least one embodiment, the irradiation object is to be arranged at a predetermined object location, e.g. in the illumination session. The predetermined object location preferably is a space region or a point in space spaced apart from the illumination device and/or the radiation emitting unit. During intended operation, the region of the irradiation object to be irradiated is located at or inside, for example completely inside, the predetermined object location. The region of the irradiation object to be irradiated is, during intended operation, also spaced apart from the illumination device and/or the radiation emitting unit.

According to at least one embodiment, the predetermined object location is arranged at a distance relative to a radiation output area of the radiation emitting unit through which the radiation generated by the at least one electromagnetic radiation source exits the radiation emitting unit during operation of the illumination device. A distance between two objects is herein defined as the shortest connection between the two objects. For example, during the illumination session, the distance between the predetermined object location and the output area is greater than or equal to one of the following values: 50 mm, 60 mm, 70 mm, 80 mm. Additionally or alternatively, the distance may be less than or equal to one of the following values: 800 mm, 700 mm, 600 mm, 500 mm, 400 mm, 300 mm, 100 mm, 80 mm. Likewise, the distance between the region of the irradiation object to be irradiated and the radiation output area may have these values during the illumination session.

In at least one embodiment, the illumination device for photodynamic therapy comprises at least one electromagnetic radiation emitting unit, the at least one electromagnetic radiation emitting unit comprising at least one electromagnetic radiation source, the electromagnetic radiation source being configured to generate radiation for the irradiation of a region of an irradiation object in an illumination session. The irradiation object is to be arranged at a predetermined object location. The predetermined object location is arranged at a distance relative to a radiation output area of the radiation emitting unit through which the radiation generated by the at least one electromagnetic radiation source exits the radiation emitting unit during operation of the illumination device.

As mentioned above, pain reduction is of crucial interest to increase acceptance levels of PDT treatment as a whole, thus increasing the use of this superior treatment. One important step to reach this goal is to increase the efficacy of PDT, e.g. by improving the homogeneity or uniformity of the irradiation of the skin, respectively. In this way, the probability that one or only a few sessions are sufficient to treat the affected skin area, is increased. Moreover, the probability of photobleaching in certain areas is also reduced if the homogeneity is increased.

With the illumination device disclosed herein, an improvement in the light dose received by the target, particularly an improvement in terms of the homogeneity of irradiation, is, inter alia, achieved, as will be explained in more detail below. For example, using several radiation sources can already improve the homogeneity.

According to at least one embodiment, the radiation emitting unit comprises a plurality of radiation sources arranged on a common radiation source carrier. The radiation source carrier is part of the radiation emitting unit. The radiation source carrier is, for example, a contiguously formed carrier. The carrier may have a continuous surface on which a plurality of radiation sources is arranged. The radiation source carrier may be self-supporting. It carries the radiation sources arranged on it.

By way of example, the radiation source carrier is platelet-shaped and comprises two opposite main sides. All radiation sources on the radiation source carrier are, for example, placed on the same main side of that carrier. In plan view on the main side, the radiation source carrier may be shaped rectangular.

According to at least one embodiment, an occupancy density of the radiation source carrier with radiation sources varies over or along the radiation source carrier.

According to at least one embodiment, an occupancy density of the radiation source carrier with radiation sources is smaller in a center region of the radiation source carrier than in peripheral regions of the radiation source carrier outside the center region. The center region and the peripheral regions are, in particular, regions of the main side of the radiation source carrier on which the radiation sources are located.

The occupancy density with radiation sources may be defined as the number of radiation sources per area. For example, the occupancy density in the peripheral regions is at least 1.2 times or at least 1.5 times or at least 2 times the occupancy density in the center region. Additionally or alternatively, the occupancy density in the peripheral regions may be at most 5 times or at most 3 times the occupancy density in the center region. The occupancy density in the center region is, for example, between $5/(100\ cm^2)$ and $50/(100\ cm^2)$ inclusive.

One major problem with PDT is the uniformity of the illumination, which can be divided in several subcategories. The first aspect is the uniformity of the provided irradiance, especially on irregular or contoured surfaces such as a human face, which pose a particular challenge. According to Lambert's cosine law, light that hits the treatment area at an angle other than 90° transfers considerably less energy to the skin. This is of special importance when treating a face, as the light emitted from a plane illumination source will always be in an oblique angle to a certain area of the face (for example the side surfaces of the nose). This usually results in an irradiance gradient which leads to a relative overexposure of certain areas while others may not get enough light at all, causing potential negative effects in regard to PDT efficacy. If not enough energy is supplied, the generation of cytotoxic singlet oxygen is not sufficiently strong, leading to reduced cell death and PDT efficacy, while the use of too much energy over a short time period may lead to photobleaching of the sensitizer, that also clearly limits treatment effects.

A configuration of light sources with lower occupancy density in a center region and higher occupancy density in peripheral regions is one possibility to increase uniformity of irradiance.

According to at least one embodiment, the radiation source carrier is a conductor carrier, such as a printed circuit board. The radiation source(s) may be electrically connected via the radiation source carrier.

According to at least one embodiment, the radiation source carrier has a metal core or metal alloy core, particularly to guide heat generated during operation of the radiation sources away from the radiation sources.

According to at least one embodiment, all radiation sources of the radiation emitting unit and/or of the illumination device are designed to generate radiation of the same or essentially the same color or peak wavelength. Peak wavelength is the wavelength, at which the emission spectrum of the light source has a global maximum. "Essentially the same" means the same within manufacturing tolerance, which is, for example, a maximum deviation of 5%. For example, a maximum deviation in the peak wavelength of the radiation sources is at most 10 nm or at most 5 nm.

According to at least one embodiment, all radiation sources of the radiation emitting unit and/or of the illumination device are configured alike. For example, the radiation sources are of the same type, comprise the same materials and/or are manufactured identically.

According to at least one embodiment, the radiation sources are arranged in a one- or two-dimensional pattern on the radiation source carrier. Particularly, in case of a two-dimensional pattern, the radiation sources of the radiation source carrier may all be located on intersection points of gridlines of a rectangular grid (pattern with a rectangular primitive cell). This means, in particular, that the center of the radiation source or of a radiation emitting chip of the radiation source lies on the respective intersection point. In case of a one-dimensional pattern, the radiation sources may all be located on a straight line.

According to at least one embodiment, the pattern is irregular. This means that the pattern changes across the source carrier. For example, the primitive translation vectors of the pattern, translating one radiation source into an adjacent one, change across the radiation source carrier. Particularly, one or both primitive translation vectors in the center region are different from the primitive translation vectors in the peripheral regions.

According to at least one embodiment, the radiation source carrier is an elongate carrier which has a main direction of extension defining a longitudinal direction.

A direction perpendicular to the longitudinal direction and parallel to a main extension plane of the radiation source carrier is called transversal direction.

For example, the distance between adjacent radiation sources measured along the longitudinal direction changes along the longitudinal direction. The distance between each pair of adjacent radiation sources measured along the transversal direction may be the same throughout the whole radiation source carrier. For example, the grid lines of the rectangular grid or the primitive translation vectors of the pattern, respectively, run parallel to the longitudinal direction and the transversal direction.

According to at least one embodiment, the center region of the radiation source carrier, in which the occupancy density is lower, is located between the peripheral regions along the longitudinal direction.

According to at least one embodiment, the pattern is symmetrical relative to one axis, e.g. along the transversal and/or longitudinal direction, or two axes, which are perpendicular to each other. For example, one of these axes is running parallel to the longitudinal direction. The other axis may run parallel to the transversal direction. The pattern may have a point symmetry with respect to a geometric center of the radiation source carrier.

According to at least one embodiment, the radiation sources on the radiation source carrier are grouped into a plurality of groups, wherein the radiation sources of each group are arranged in a regular group pattern, wherein at least two groups of the plurality of groups have different group patterns. In a regular pattern, the primitive translation vectors do not change across the entire group. Different group patterns are, for example, different from each other in terms of one or two primitive translation vectors. For example, each radiation source on the radiation source carrier is assigned to one group.

According to at least one embodiment, at least two groups, particularly all groups, have the same number of radiation sources.

According to at least one embodiment, each group has a plurality of radiation sources, for example between four and 40, inclusive, or between ten and 25, inclusive.

According to at least one embodiment, at least two groups of the plurality of groups have the same group pattern. Particularly, the primitive translation vectors are the same in the two groups.

According to at least one embodiment, a first group with a first group pattern is arranged between a second group and a third group when seen in plan view of the radiation source carrier. For example, the first group is located between the second group and the third group along the longitudinal direction. For example, each radiation source of the radiation source carrier is assigned to one of the three groups.

According to at least one embodiment, the second and the third group have the same group pattern and the first group has a different group pattern. Particularly, the first group is assigned to the center region and/or has a lower occupancy density with radiation sources and the second and third groups are assigned to the peripheral regions and/or have a higher occupancy density with radiation sources. The values for the relative difference in the occupancy density mentioned above for the center region and the peripheral regions may likewise hold for the first group and the second and third groups.

According to at least one embodiment, the group patterns of the groups are one-dimensional or two-dimensional.

According to at least one embodiment, the groups each comprise one or a plurality of rows of radiation sources. For example, the groups comprise between two and five rows, inclusive. The rows may extend parallel to the transversal direction.

According to at least one embodiment, the groups each comprise one or a plurality of columns of radiation sources. For example, the groups comprise between four and ten columns, inclusive. The columns may extend parallel to the longitudinal direction.

According to at least one embodiment, at least two groups or all groups comprise the same number of radiation sources. For example, the second and the third group comprise the same number of radiation sources. The first group may comprise the same number of radiation sources.

According to at least one embodiment, the distance between two adjacent groups is greater than a characteristic distance, for example the maximum distance, the minimum distance or the average distance, between two rows of radiation sources and/or greater than a characteristic distance between two columns of radiation sources in one or both adjacent groups. The distance between two adjacent groups may be the smallest distance between two radiation sources of these two adjacent groups.

For example, the distance between each pair of adjacent radiation sources within one group is between 5 mm and 40 mm, inclusive. The distance between two adjacent groups is, for example, between 20 mm and 80 mm, inclusive.

According to at least one embodiment, the radiation source carrier has a carrier edge, wherein the carrier edge delimits the radiation source carrier, for example in the longitudinal direction and/or in the transversal direction.

According to at least one embodiment, the distance between the group closest to the carrier edge and the carrier edge is less than the distance between two adjacent radiation sources of this group, which are arranged one behind the other in a direction away from the carrier edge. The distance between the carrier edge and the group is defined by the distance between the carrier edge and the radiation source of the group lying closest to the carrier edge.

According to at least one embodiment, the distance between the group closest to the carrier edge and the carrier edge is less than the distance between two adjacent radiation sources of this group, which adjacent radiation sources are arranged one behind the other or sequentially in a direction along the carrier edge, which might be the longitudinal direction.

According to at least one embodiment, the radiation emitting unit comprises a unit housing which defines an outer edge of the radiation emitting unit. For example, the outer edge delimits the radiation emitting unit in the transversal direction. The housing may comprise or consist of a metal or plastic. The radiation source carrier is, for example, mechanically connected to the unit housing and carried by the unit housing. When viewed in plan view of a main side of the radiation source carrier, the unit housing may completely surround the radiation source carrier, e.g. laterally.

According to at least one embodiment, the radiation emitting unit comprises a plurality of radiation source carriers, each radiation source carrier being provided with a plurality of radiation sources. All features disclosed so far and in the following in connection with one radiation source carrier are likewise disclosed for all or some radiation source carriers of the radiation emitting unit and/or the illumination device. The radiation source carriers are, for example, arranged such that main directions of extension of the radiation source carriers run parallel to each other. For example, the radiation source carriers are arranged one behind the other along the transversal direction running perpendicularly to the longitudinal direction.

According to at least one embodiment, the radiation source carrier closest to the outer edge is oriented such that a main radiation direction of the radiation sources on this radiation source carrier is outwardly offset from or outwardly tilted relative to a main radiation direction of the radiation sources on another radiation source carrier further away from the outer edge. A main radiation direction is the direction in which the radiant or luminous intensity has a global maximum. "Outwardly offset" particularly means that the main radiation direction of the radiation sources of the radiation source carrier closest to the outer edge is more strongly tilted towards the outer edge than the main radiation direction of the radiation sources of the another radiation source carrier. For example, the main radiation direction of the radiation sources of the radiation source carrier closest to the outer edge is tilted with respect the main radiation direction of the radiation sources of the another radiation source carrier by at least 5° or at least 10° or at least 20° towards the outer edge. In other words, the main emission directions of the radiation sources on the different radiation source carriers of the radiation emitting unit may vary. The closer to the outer edge the more the main radiation direction may be tilted towards the outer edge and/or away from the main radiation direction of radiation sources on a more centrally arranged radiation source carrier.

According to at least one embodiment, the distance between two adjacent radiation sources of the radiation emitting unit, particularly between each pair of two adjacent radiation sources of the radiation emitting unit is greater than or equal to one of the following values: 5 mm, 10 mm, 15 mm.

According to at least one embodiment, the distance between two adjacent radiation sources of the radiation emitting unit, particularly between each pair of two adjacent radiation sources of the radiation emitting unit is less than or equal to one of the following values: 40 mm, 35 mm, 30 mm, 25 mm, 20 mm.

According to at least one embodiment, an area on the radiation source carrier occupied with radiation sources is at least 200 cm$^2$ or at least 300 cm$^2$. Additionally or alternatively, the area is at most 600 cm$^2$ or at most 500 cm$^2$. For example, the area is at most 28 cm×16 cm and/or at least 22 cm×10 cm, e.g. 26 cm×12 cm. The area is limited or defined by the positions of the outermost radiation sources.

According to at least one embodiment, the radiation emitting unit comprises one continuous radiation source carrier common for all radiation sources of the radiation emitting unit.

According to at least one embodiment, the area of the surface of the radiation source carrier is at least 300 cm$^2$ and/or at most 600 cm$^2$. For example, the area is at least 24 cm×14 cm and/or at most 30 cm×18 cm, e.g. 28 cm×16 cm. The surface of the radiation source carrier is the surface on which the radiation sources are arranged.

According to at least one embodiment, at least two, e.g. adjacent, radiation source carriers of the radiation emitting unit are arranged angled relative to one another. Particularly, vertical axes of the carriers, running perpendicularly to main extension planes of the carriers, are angled relative to one another. By way of example, the angle between the vertical axes of two radiation source carriers is at least 5° at least 10° or at least 20°. Particularly, the vertical axes of a radiation source carrier runs parallel or essentially parallel to the main radiation direction of the radiation sources of this radiation source carrier.

According to at least one embodiment, the radiation source carriers of the radiation emitting unit are fixed in their relative position to one another. Alternatively, the radiation source carriers of the radiation emitting unit may be movable, in particular tiltable, relative to one another. The movement relative to one another may be performed manually. Alternatively, the radiation emitting unit may comprise one or more actuators assigned to the radiation source carriers and configured to move the radiation source carriers. The actuators may be controllable by an electronic control unit of the illumination device. In this way an automatic movement of the radiation source carriers relative to one another may be realized.

According to at least one embodiment, the at least one radiation source is an optoelectronic component, for example a light emitting diode (LED) and/or a surface mountable component. All features disclosed so far and in the following for the at least one radiation source are likewise disclosed for all or some radiation sources of the illumination device.

According to at least one embodiment, the optoelectronic component comprises a semiconductor chip. The optoelectronic component may comprise exactly one semiconductor chip. The semiconductor chip may be based on a III-V-compound semiconductor material, like AlGaInN or AlGaInP or AlGaInAs or binary or ternary subsystems thereof. The semiconductor chip may be a surface emitter, particularly a so-called thin-film chip, where the growth substrate of the semiconductor material is removed. Alternatively, the semiconductor chip may be a so-called volume emitter, where the growth substrate is still part of the semiconductor chip.

According to at least one embodiment, the optoelectronic component comprises a chip carrier on which the semiconductor chip is arranged. The chip carrier may be pierced by through connections, electrically connecting the semiconductor chip on the front side of the chip carrier with contact pads on the rear side of the chip carrier.

According to at least one embodiment, the chip carrier comprises a ceramic material, like AlN or $Al_2O_3$. This is advantageous in terms of heat dissipation.

According to at least one embodiment, the chip carrier is a cavity-free or plane chip carrier. In this case, the chip carrier does not laterally surround the semiconductor chip.

According to at least one embodiment, the semiconductor chip is embedded in an encapsulation. The encapsulation may comprise silicone or epoxy or resin or consist thereof. The semiconductor chip may be laterally surrounded by the encapsulation. The encapsulation may cover a radiation exit surface of the semiconductor chip. The radiation exit surface faces away from the chip carrier.

According to at least one embodiment, the encapsulation is lens-shaped. Particularly, the encapsulation may be shaped such that it collimates the light or radiation emitted by the semiconductor chip. For example, the encapsulation reduces the opening angle of the emitted radiation/light.

According to at least one embodiment, the semiconductor chip is a light-emitting diode chip (LED-chip).

According to at least one embodiment, the optoelectronic component has lateral dimensions of at most 5 mm×5 mm. A thickness of the optoelectronic component is, for example, at most 4 mm.

According to at least one embodiment, the optoelectronic component has a luminous efficacy of greater than or equal to one of the following values: 60 lm/W, 70 lm/W, 75 lm/W, 80 lm/W, 85 lm/W, 90 lm/W, 100 lm/W. Additionally or alternatively the luminous efficacy is smaller than or equal to one of the following values: 200 lm/W, 180 lm/W, 160 lm/W, 140 lm/W, 1201 m/W. For example, the luminous efficacy is between 100 lm/W and 120 lm/W inclusive. For example, the luminous efficacy is measured at an operating current of 350 mA. The luminous efficacy is defined as the ratio between the luminous flux $\Phi_v$ and the radiant flux $\Phi_e$.

According to at least one embodiment, for intended operation, the optoelectronic component is operated with an operating current greater than or equal to one of the following values: 400 mA, 450 mA, 500 mA, 550 mA, 600 mA, 750 mA, 850 mA, 950 mA.

According to at least one embodiment, for intended operation, the optoelectronic component is operated with an operating current less than or equal to one of the following values: 1300 mA, 1200 mA, 1100 mA, 1000 mA, 900 mA, 850 mA, 800 mA, 750 mA, 700 mA, 650 mA, 600 mA.

According to at least one embodiment, the radiation emitting unit comprises a number of radiation sources or optoelectronic components which is greater than or equal to any one the following numbers: 20, 25, 30, 35, 40, 45.

According to at least one embodiment, the radiation emitting unit comprises a number of radiation sources or optoelectronic components which is less than or equal to any one the following numbers: 60, 55, 50, 45.

According to at least one embodiment, the emission characteristics or the radiant intensity of the optoelectronic component has a maximum at an emission angle of less than 20° or less than 10° or less than 5°, for example at 0°. The angle is particularly measured with respect to an axis running perpendicularly to a main extension plane of the optoelectronic component or a main extension plane of the respective semiconductor chip.

According to at least one embodiment, the optoelectronic component emits a major part of its radiant power, for example at least 50% or at least 75% or at least 90% of its radiant power, under an opening angel (emission angle range) of less than or equal to 90° or 85° or 80°.

According to at least one embodiment, the emission spectrum of the optoelectronic component has a peak wavelength in one of the following ranges: 634 nm±4 nm, 635±5 nm, 542 nm±4 nm, 506 nm±4 nm. Particularly, this peak wavelength is obtained at an operating temperature of the optoelectronic component below 50° C., for example at 25° C., and at operating currents between 100 mA and 1000 mA, inclusive. The half-band width of the spectrum is, e.g. at least 10 nm and/or at most 20 nm, e.g. 16 nm.

According to at least one embodiment, a maximum temperature induced variation of the peak wavelength of the emission spectrum of the optoelectronic component is less than or equal to one of the following values: 15 nm, 12 nm, 10 nm. This applies for a temperature range from −40° C. to 130° C. and at an operating current of 350 mA.

According to at least one embodiment, a temperature induced maximum variation in the relative luminous flux $\Phi_v/\Phi_v$ (25° C.) of the optoelectronic component is less than or equal to one of the following values: 1.0, 0.9. This applies for a temperature range from −40° C. to 130° C. and at an operating current of 350 mA.

In fact, another aspect which interferes with a uniform illumination is the ability of radiation sources to emit light of the same wavelength and irradiance throughout a complete treatment duration. In the case of a light-emitting diode (LED) for example, with changes of the LED temperature, the light emission properties may shift in either direction, meaning one of or both of the radiant flux and the peak emission wavelength may increase or decrease, depending on the exact type of the LED. A change of the radiant flux may result in a change of the irradiance and this might have potential negative effects due to the same reasons as described above. A shift of the wavelength could move the emission spectrum away from the absorption band of, e.g. PpIX which would in turn have the same results as a shortage of delivered energy. Due to an insufficient amount of absorbed energy by PpIX, the formation of cytotoxic singlet oxygen is also decreased with the same negative consequences for the treatment success.

According to at least one embodiment, the radiation source has a bandwidth (Full Width Half Maximum, FWHM) of the emission peak with the peak wavelength which is at most 30 nm or at most 25 nm or at most 20 nm. Additionally or alternatively, the bandwidth is at least 5 nm or at least 10 nm.

According to at least one embodiment, the radiation output area of the radiation emitting unit is a discontinuous area which is composed of the radiation output surfaces of the optoelectronic components. This means, that the radiation output area is not a homogenous emission surface but rather comprises several spatially separated emission spots assigned to the radiation sources, where the radiation is emitted. In the region of the radiation output area between the radiation spots, less radiation, for example no radiation, is emitted.

According to at least one embodiment, the radiation output area is formed by a cover plate of the radiation emitting unit covering all radiation sources of the radiation emitting unit, especially when viewed in plan view of the cover plate. The cover plate is, for example, formed of a transparent material, like glass or plexiglass, e.g. of casted plexiglass. The cover plate may form a heat shield for a patient. The heat shield may absorb or deflect heat radiation emitted by the radiation source(s) and thus protect the patient from this heat. The cover plate may have a thickness of 2 mm±0.6 mm.

According to at least one embodiment, the illumination device comprises a plurality of radiation emitting units which are movably connected to one another. For example, the radiation emitting units are pivotally connected to each other. For example, they are connected to each other via hinges.

According to at least one embodiment, the plurality of radiation emitting units is linearly connected. This means that the radiation emitting units are arrange one behind the other along a line.

According to at least one embodiment, a pivot axis around which the radiation emitting units are pivotable relative to one another is parallel or essentially parallel to the longitudinal direction, defined by the main direction of extension of one radiation source carrier. "Essentially parallel" means, for example, that they are tilted to each other by at most 5° or at most 2°.

According to at least one embodiment, the radiation emitting units are aligned such that the main directions of extension of the radiation source carriers of the respective radiation emitting units are parallel to one another. Preferably all main directions of extension of the radiation source carriers of one radiation emitting unit or of all radiation emitting units are parallel or essentially parallel to each other.

According to at least one embodiment, the radiation emitting units are connected such that a radiation emitting unit can be pivoted relative to an adjacent radiation emitting unit by at least 20° at least 30° or at least 45° or at least 60° or at least 90°. Additionally or alternatively, a radiation emitting unit can be pivoted relative to an adjacent radiation emitting unit by at most 170° or at most 150°.

According to at least one embodiment, all of the radiation emitting units of the illumination device are configured identically. This means identically within the limits of manufacturing tolerances, of course. For example, all radiation emitting units comprise the same number of radiation source carriers, the same number of radiation sources and the same type of radiation sources, e.g. emitting radiation with the same or essentially the same peak wavelength.

According to at least one embodiment, the illumination device comprises three or more, for example four or more, such as five or more, radiation emitting units.

According to at least one embodiment, the radiation emitting units are connected to one another such that the radiation emitting units can be moved relative to one another in order to adjust the illumination device for irradiating a surface of a non-plane shape, where the shape of different surfaces to be illuminated may vary. For example, the illumination device can be adjusted for irradiating a surface of cylindrical shape or a human head, which may be idealized. The radiation emitting units can then be arranged such that the radiation output areas of the radiation emitting units have all the same distance to a lateral surface of the cylinder defining the cylindrical shape.

According to at least one embodiment, the radiation emitting units can be arranged in a C-shape configuration and/or a semi-circle configuration. Particularly, they may all emit radiation on the irradiation object, when in the C-shape or semi-circle configuration. The radiation of the radiation emitting units may overlap in the object location. In the C-shape configuration or semi-circle configuration, respectively, the angle between two adjacent radiation emitting units may be at least 100° or at least 110° and/or at most 150° or at most 130°, e.g. 120°. Such a configuration may result in a more homogeneous illumination, e.g. of a human face.

The angle between two radiation emitting units is, in particular, defined as the angle between the output areas and/or the radiation source carriers of the two radiation emitting units.

For example, a first radiation emitting unit constitutes a center radiation emitting unit. A second and a third radiation emitting unit may be arranged adjacent to the first radiation emitting unit on the left and right side, i.e. on opposite sides, of the first radiation emitting unit, respectively, and may be configured to be arranged such that they are tilted towards each other, e.g. so that main radiation axes of the second and third radiation emitting units cross, e.g. in the object location. The value of the angle between the second and the first radiation emitting unit may be the same as the value of the angle between the third and the first radiation emitting unit. A fourth radiation emitting unit may be arranged adjacent to the second radiation emitting unit on the left side of the second radiation emitting unit, i.e. on the side remote from the first radiation emitting unit. A fifth radiation emitting unit may be arranged adjacent to the third radiation emitting unit on the right side of the third radiation emitting unit, i.e. on the side remote from the first radiation emitting unit. The first, second and third radiation emitting units may therefore be arranged between the fourth and the fifth radiation emitting units. The fourth and the fifth radiation emitting units may be configured to be arranged such that they are tilted towards each other so that main radiation axes of the fourth and fifth radiation emitting unit cross, e.g. in the object location. The value of the angle between the fourth and the first radiation emitting unit may be the same as the value of the angle between the fifth and the first radiation emitting unit. However, this value may be different, e.g., smaller, than the value of the angle between the second and the first radiation emitting unit or between the third and the first radiation emitting unit. The fourth and fifth radiation emitting unit may be more tilted/may have smaller angles with respect to the first radiation emitting unit than the second and third radiation emitting unit. For example, the output areas of the fourth and fifth radiation emitting unit may be closer to a parallel arrangement than the output areas of the second and the third radiation emitting units or they may be arranged parallel.

According to at least one embodiment, the minimum angle which can be set between the fourth and the second radiation emitting unit and between the third and fifth radiation emitting unit is between 60° and 80°, e.g. about 68°.

According to at least one embodiment, in the C-shape configuration and/or in the semi-circle configuration, the distance, e.g. the maximum distance or the average distance, between the output areas of the fourth and fifth radiation emitting unit is at least 30 cm or at least 35 cm and/or at most 50 cm or at most 55 cm. For example, the distance is 39 cm.

According to at least one embodiment, the radiation emitting unit comprises one or more electronic control units for controlling the operation of the illumination device.

According to at least one embodiment, the illumination device comprises a motor configured to move the radiation emitting unit, e.g. relative to a mount of the radiation emitting unit, relative to another radiation emitting unit of the illumination device, and/or relative to the illumination object. For example, the illumination device comprises several motors, each uniquely assigned to one radiation emitting unit. The motor or the motors are configured to move the radiation emitting units relative to one another and/or relative to the illumination object, in particular in order to adjust the illumination device for irradiating a surface of a non-plane shape homogenously.

In order to move the radiation emitting units with help of the motor or the motors, an electronic control unit of the illumination device may be operatively coupled to the motors and configured to operate the motors according to a preselected arrangement of the radiation emitting units.

According to at least one embodiment, the radiation emitting units are selectively activatable to emit radiation in the illumination session. In other words, the radiation emitting units can be turned on and off individually and independently from one another. Preferably, also the radiation intensity emitted by the radiation emitting units (and, hence, the irradiance of the region of the illumination object illuminated by the respective unit) can also be set individually for each radiation emitting unit independently of the other radiation emitting units.

In order to realize this, an electronic control unit of the illumination device may be operatively coupled to the radiation emitting units and configured to activate the radiation emitting units, particularly the radiation sources, according to a predetermined irradiation pattern.

The second aspect which is important in respect to irradiance uniformity is the distance of the illumination device and the irradiation object. For example, during the treatment of irregular or contoured surfaces like the human face, the outer regions of the light emitting surface of a plane illumination device are further away from the irradiation object than a spot located directly in the center of the light emitting surface. This can be mitigated by a curved light emitting surface which then in turn causes illumination deficits when illuminating a plane treatment area. However, even when using a curved light emitting surface, it is still very likely that either the patient is not correctly placed by the operating personnel at the start of the treatment or illumination session or that the patient moves during the treatment. Both scenarios lead to incorrect treatment distances that may negatively affect the treatment efficacy.

By using several radiation emitting units, which can even be moved relative to each other, a non-plane surface, like the human face, can be treated more homogeneously. Furthermore, displacements of the patient during or before the treatment can be corrected during the treatment or the illumination session.

According to at least one embodiment, the illumination device comprises a location or distance monitoring system. The monitoring system is configured to monitor the location and/or the distance of the irradiation object from the radiation emitting unit and/or from the predetermined object location. One distance monitoring system may be assigned to each radiation emitting unit.

According to at least one embodiment, the monitoring system comprises a distance sensor arranged on the radiation source carrier of the at least one radiation emitting unit. Particularly, each radiation emitting unit of the illumination device may comprise at least one distance sensor assigned to the respective radiation emitting unit. The distance sensor may be arranged on the radiation source carrier. All features disclosed for one distance sensor are likewise disclosed for some or all distance sensors of the illumination device.

The distance sensor is, for example, a time-of-flight sensor. The distance sensor may comprise a laser diode, like a VCSEL, a radiation receiving sensor element and a micro controller.

According to at least one embodiment, the distance sensor is located offset of a geometric center of the radiation source carrier when viewed in plan view of a main side or the radiation source carrier. Particularly, in plan view, a radiation source overlaps with the geometric center of the radiation source carrier. The distance sensor is, for example, offset from the geometric center by at most 40 mm and/or at least 5 mm. For example, the distance sensor is located between a radiation source at the geometric center of the radiation source carrier and a radiation source closest to the radiation source in the geometrical center, when viewed in plan view of the main side.

According to at least one embodiment, the distance monitoring system comprises an electronic control unit. The electronic control unit may be a microcontroller. The electronic control unit may be operatively coupled to the motor or the motors of the illumination device and may be configured to operate the motors in order to change relative positions of the radiation emitting units. Additionally, the electronic control unit may be operatively coupled to the radiation sources of the radiation emitting units and may be configured to operate the radiation sources in order to change the radiant power emitted by the radiation sources.

Thus, the same electronic control unit may be used for controlling the motors and the selective activation of the radiation emitting units. Alternatively, there may be several control units, at least one for controlling the motors and at least one for selectively activating the radiation emitting units.

According to at least one embodiment, the illumination device is configured to compensate for distance or location variations of the irradiation object from the respective radiation emitting unit and/or the predetermined object location in order to maintain a predetermined radiation or light dose during the illumination session. Preferably, in this way, the distance between the respective unit and the illumination object may be kept constant. The terms radiation dose and light dose are herein used as equivalents.

For example, the illumination device is operated as follows:

an irradiation object, such as a human being, is irradiated by the illumination device, a variation of the irradiation object from a radiation emitting unit is measured with help of the distance sensor of the radiation emitting unit, the measurement signal is processed and the electronic control unit generates a corresponding operation signal for operating the motor assigned to the radiation emitting unit so that the distance or location variation is compensated.

According to at least one embodiment, the distance monitoring system is configured to adjust the operation of the illumination device or to call for an adjustment of the operation of the illumination device by using one of, an arbitrary combination of or all of the following measures:

varying the distance between the respective radiation emitting unit and the irradiation object, adjusting the radiation power emitted by the respective radiation emitting unit, and/or adjusting a duration of the illumination session.

Particularly, a distance or location variation of the irradiation object is measured by the one or the plurality of distance sensors of the radiation emitting units. The measurement signals indicative for the distance or location variation are processed and corresponding operation signals are produced with which the electronic control unit accordingly automatically operates the motors assigned to the radiation emitting units or the radiation sources of the radiation emitting units.

According to at least one embodiment, during the illumination session, the distance between the radiation output area of a radiation emitting unit and the object location or the region of the irradiation object to be irradiated is kept at values less than or equal to one of the following values: 20 cm, 15 cm, 10 cm, 8 cm, 7 cm, 6 cm, 5 cm. Alternatively or additionally, the respective distance is kept at values greater than or equal to one of the following values: 1 cm, 2 cm, 3 cm, 4 cm, 5 cm. For example, the optimum distance, also referred to as nominal distance, may be 12 cm±1.0 cm or 12.5 cm±1.5 cm.

According to at least one embodiment, the area of the irradiation object illuminated by the radiation emitting units of the illumination device (the illuminated area), when the radiation emitting units are at the nominal distance to the irradiation object, is between 400 cm$^2$ and 1000 cm$^2$, inclusive. For example, the illuminated area is at most 32 cm×26 cm and/or at least 26 cm×20 cm, e.g. 29 cm×23 cm. Particularly, this may hold for the illumination device being in the C-shape configuration or the semi-circle configuration. Particularly, this holds when all radiation emitting units of the illumination device emit radiation and are each at the nominal distance. The illuminated area is, in particular, the area in which the irradiance caused by the radiation emitting units is at least 50% or at least 75% of the maximum irradiance caused by the radiation emitting units.

According to at least on embodiment, the entire illumination session is less than or equal to one of the following values: 20 min, 19 min, 18 min, 17 min, 16 min, 15 min, 14 min, 13 min. Session durations up to 20 minutes are usually accepted by users. Additionally or alternatively, the duration of the entire illumination session is greater than or equal to one of the following values: 10 min, 11 min, 12 min, 13 min. The duration of the session may be between 10 min and 20 min, for example, e.g. 18 minutes.

According to at least one embodiment, the illumination device is configured to irradiate the region of the irradiation object with a predetermined light dose during the illumination session. The light dose may be greater than or equal to one of the following values when the irradiation object is arranged at the object location, particularly at the nominal distance to the radiation emitting unit(s), during the illumination session: 30 J/cm$^2$, 35 J/cm$^2$, 37 J/cm$^2$. Alternatively or additionally, the light dose may be less than or equal to one of the following values when the irradiation object is arranged at the object location during the illumination session: 45 J/cm$^2$, 40 J/cm$^2$, 37 J/cm$^2$. The mean or maximum irradiance may be greater or equal to one of the following values when the irradiation object is arranged at the object location (nominal distance) during the illumination session: 25 mW/cm$^2$, 40 mW/cm$^2$, 50 mW/cm$^2$. Alternatively or additionally, the mean or maximum irradiance may be smaller or equal to one of the following values when the irradiation object is arranged at the object location (nominal distance) during the illumination session: 75 mW/cm$^2$, 65 mW/cm$^2$, 60 mW/cm$^2$. For example, the mean or maximum irradiance when the irradiation object is arranged at the object location during the illumination session is 62 mW/cm$^2$ or 61 mW/cm$^2$. The values above particularly hold at least for red light, e.g. with a peak wavelength at 634 nm±4 nm at 25° C.

A sufficient light dose is one of the key requirements to successfully carry out PDT. However, when choosing the light dose, the maximum tolerable level of pain for the patient must also be taken into account. The range between a light dose of 30 and 45 J/cm$^2$, in particular a light dose of 37 J/cm$^2$, may be considered the best compromise between adequate treatment efficiency and pain burden, e.g. when using red light. Additionally or alternatively, a mean or maximum irradiance between 25 mW/cm$^2$ and 75 mW/cm$^2$, particularly a mean or maximum irradiance of 62 mW/cm$^2$ may be considered the best compromise between adequate treatment efficiency and pain burden, e.g. when using red light.

According to at least one embodiment, the illumination device is configured to irradiate the region of the irradiation object with a predetermined light dose during the illumination session. The light dose may be greater than or equal to one of the following values when the irradiation object is arranged at the object location during the illumination session: 8 J/cm$^2$, 9 J/cm$^2$, 10 J/cm$^2$. Alternatively or additionally, the light dose may be less than or equal to one of the following values when the irradiation object is arranged at the object location during the illumination session: 12 J/cm$^2$, 11 J/cm$^2$, 10 J/cm$^2$. The values above particularly hold at least for blue light.

The range between a light dose of 8 and 12 J/cm$^2$, in particular a light dose of 10 J/cm$^2$, may be considered the best compromise between adequate treatment efficiency and pain burden, e.g. when using blue light.

According to at least one embodiment, the illumination device comprises a feedback system which is configured to provide feedback in order to assist in keeping the irradiation object, for example a patient, in the predetermined object location, close to the predetermined object location and/or at a predetermined distance relative to the respective radiation emitting unit. The feedback system is, for example, operatively coupled to the monitoring system.

According to at least one embodiment, the feedback system is configured to issue visual, audible and/or tactile feedback to the patient or an operator of the illumination device which indicates whether the current object location is sufficiently close to the predetermined object location or whether adjustment is required. For example, the illumination device comprises a display and/or a loudspeaker for giving visual and/or audible feedback. For example, the visual or audible or tactile feedback asks the patient to move and/or asks an operator to adjust the positions of the radiation emitting unit(s) or the radiation power emitted by the radiation emitting unit(s).

The feedback system may be operated in addition or as an alternative to the automatic adjustment of the distance between the respective radiation emitting unit and the irradiation object and the radiation power emitted by the respective radiation emitting.

According to at least one embodiment, the illumination device is configured such that the radiation emitting unit can be switched on, e.g. via a user interface, particularly via the display. For example, the operator has to operate or press a switch-on button. The button may also be a region on a touch display, i.e. a virtual button. The illumination device may be configured such that each radiation emitting unit of the illumination device may be switched on separately and/or independently or all radiation emitting units can only be switched on together and/or simultaneously. The illumination device may also be configured such each of the radiation emitting units can be switch off separately and/or individually after having been switched on.

When switched on, the distance sensor of the radiation emitting unit may be activated in order to measure the distance to the irradiation object. When switched on, the radiation emitting unit may be operable in at least three modes, e.g. a no-intensity mode (or distance monitoring mode), a low-intensity mode and a nominal-intensity mode, the different modes being modes in which the radiation emitting unit emits different radiation intensities or no intensity in case of the no-intensity mode. When the radiation emitting unit is switched on it may, by default, be in the no-intensity mode. In the no-intensity mode, only the distance monitoring system may be operable. The distance sensor may continuously poll for objects within a predetermined distance from the unit in that mode.

According to at least one embodiment, the illumination device is configured such that the radiation emitting unit is operable in the low-intensity mode when the distance of the radiation emitting unit to the irradiation object lies within an irradiation range around the nominal distance. In the low-intensity mode, the assigned distance sensor may be activated. The irradiation range may be, e.g., ±2.0 cm or ±1.5 cm around the nominal distance. The nominal distance may be, e.g., 12.0 cm or 12.5 cm. The distance between a radiation emitting unit and the irradiation object is, in particular, defined as the distance of the output area to the irradiation object.

By way of example, the radiation emitting unit is only operable in the low-intensity mode when the distance of the radiation emitting unit to the irritation object lies within the irradiation range. If the distance does not lie in the irradiation range, the radiation emitting unit may not be switchable or may not switch into the low-intensity mode or in any other mode in which radiation is emitted.

According to at least one embodiment, the low-intensity mode is a mode in which the radiation intensity emitted by the radiation emitting unit is smaller than a nominal radiation intensity used during the illumination session. For example, in the low-intensity mode, the radiation intensity is at most 50% or at most 25% or at most 10% or at most 5% of the nominal radiation intensity. Additionally or alternatively, the radiation intensity in the low-intensity mode is at least 0.5% or at least 1% or at least 5% or at least 10% of the nominal radiation intensity. Particularly, the radiation intensity in the low-intensity mode is sufficient to see an illuminated area on the irradiation object caused by the radiation emitting unit on the irradiation object. For example, the radiation emitted in the low intensity mode is so small that the patient does not feel any pain, whereas noticeable pain may be experienced in the nominal-intensity mode.

The nominal radiation intensity is particularly the radiation intensity which results in the mean or maximum irradiance of the irradiation object during the illumination session specified above when the irradiation object is at the object location or at the nominal distance, respectively.

According to at least one embodiment, the illumination device is configured such that the at least one radiation emitting unit is switched or is switchable from the low-intensity mode into the no-intensity mode when the distance of the radiation emitting unit to the irradiation object leaves the irradiation range. For example, the radiation emitting unit is then automatically switched from the low-intensity mode into the no-intensity mode. Likewise, the radiation emitting unit may switch automatically from the no-intensity mode into the low-intensity mode when the distance is in the irradiation range.

According to at least one embodiment, the no-intensity mode is a mode in which the radiation emitting unit does not emit radiation. However, in the no-intensity mode, the distance sensor of the radiation emitting unit may still be switched on in order to measure the distance to the irradiation object, e.g. by performing measurements in specific intervals.

The illumination device may be configured such that, if the distance of one radiation emitting unit to the irradiation object leaves the irradiation range, only this radiation emitting unit is switched into the no-intensity mode or several or all radiation emitting units are switched into the no-intensity mode, e.g. regardless whether they are in the irradiation range or not.

According to at least one embodiment, the illumination device is configured such that the at least one radiation emitting unit is switchable from the low-intensity mode and/or the no-intensity mode into the nominal-intensity mode. The nominal-intensity mode is, in particular, a mode in which the radiation intensity is the nominal intensity. For example, the radiation emitting unit is only switchable from the no-intensity mode and/or the low-intensity mode into the nominal-intensity mode when the distance between the radiation emitting unit and the irradiation object is in the irradiation range. Alternatively, the radiation emitting unit may be switchable from the no-intensity mode and/or the low-intensity mode into the nominal-intensity mode regardless whether the distance is or is not in the irradiation range. In this second case, when the radiation emitting unit is switched in the nominal-intensity mode, a warning signal may be generated in order to warn a user that the radiation emitting unit is not in the irradiation range.

Alternatively, the radiation emitting unit may only be switchable into the nominal-intensity mode when starting from the low-intensity mode. For example, in this case, the nominal-intensity mode may not be directly reachable from the no-intensity mode.

The illumination device may be configured such that each radiation emitting unit is switchable into the nominal-intensity mode, e.g. regardless of the mode of the other radiation emitting units. For example, all radiation emitting units are simultaneously switchable into the nominal-intensity, e.g. by pressing a start button, regardless of whether all of them are in the respective irradiation range or not or regardless of the mode of the radiation emitting units.

Alternatively, a radiation emitting unit may only be switchable into the nominal intensity mode if several or all radiation emitting units of the illumination device, particularly those which have been switched on, are in their respective low-intensity mode and/or have a distance to the irradiation object in the irradiation range.

Switching a radiation emitting unit into the nominal-intensity mode may be done manually by the operator, e.g. by operating an element of the user interface, like a start button, which again may be a region on a touch display. Operating the element may simultaneously switch all radiation emitting units into the nominal-intensity mode.

For example, the illumination device is configured such that, when switching a radiation emitting unit on, it is automatically either switched into the no-intensity mode or into the low-intensity mode, depending on the distance between the irritation object and the radiation emitting unit when being switched on.

Next, a method for treating a skin disease is specified. The illumination device specified herein is expediently used for this method. All features disclosed in connection with the illumination device are therefore also disclosed for the method and vice versa.

According to at least one embodiment, the method comprises a step a), in which a pharmaceutical substance is applied to the surface of the skin in a region which is to be treated. In a step b), the skin region to be treated is arranged in a predetermined object location of the illumination device according to any of the embodiments described herein. In a step c), the skin region to be treated is irradiated with the illumination device. In this step, the illumination session is executed.

The skin disease or disorder may be or may comprise a neoplastic skin disease, like actinic keratosis, basal cell carcinoma, squamous cell carcinoma in situ, warts, acne, wound healing disorders/chronic wounds, bacterial and/or fungal infections or inflammatory skin diseases. It should be noted that the present disclosure covers non-therapeutic methods. For example, the pharmaceutical substance is suitable to be topically applied to the skin in a region to be treated.

According to at least one embodiment, the pharmaceutical substance is a photosensitizing drug or precursor to such a drug that is excitable by light in the radiation spectrum emitted by the illumination device.

According to at least one embodiment, the pharmaceutical substance comprises 5-aminolevulinic acid. 5-aminolevulinic acid has been well studied and is considered a reliable prodrug for generating a photosensitizer.

According to at least one embodiment, the skin disease is a neoplastic skin disease like actinic keratosis, basal cell carcinoma, squamous cell carcinoma in situ, or warts, acne, wound healing disorders/chronic wounds, bacterial and/or fungal infections, inflammatory skin diseases.

According to at least one embodiment, the method comprises:
providing a measurement signal which is indicative for a distance between the radiation emitting unit and the radiation object,
generating an operation signal as a function of the measurement signal, said operation signal being configured to cause the illumination device to adjust the operation of the illumination device or to call or to trigger a call for an adjustment of the operation of the illumination device. Adjusting the operation may comprise one or more of:
varying the distance between the respective radiation emitting unit and the irradiation object,
adjusting the radiation power emitted by the respective radiation emitting unit, and/or
adjusting a duration of the illumination session.

According to at least one embodiment, the method for operating an illumination device comprises the execution of a start sequence prior to the illumination session.

According to at least one embodiment, the execution of the start sequence comprises switching on the radiation emitting unit such that the assigned distance sensor is activated for measuring the distance to the irradiation object (step S1). The switching on may be performed by an operator, e.g. by operating a switch-on button, e.g. on a touch display.

According to at least one embodiment, the execution of the start sequence comprises adjusting the distance of the radiation emitting unit to the irradiation object until the distance is within the irradiation range (step S2). Adjusting the distance may be done manually by the operator, e.g. by manually moving the radiation emitting unit and/or the irradiation object.

According to at least one embodiment, the execution of the start sequence comprises operating the radiation emitting unit in the low-intensity mode in order to illuminate the irradiation object with a low radiation intensity, when the distance is in the irradiation range (step S3).

According to at least one embodiment, the execution of the start sequence comprises adjusting the position of the irradiation object relative to the illumination device while maintaining the distance of the radiation emitting unit to the irradiation object in the irradiation range (step S4).

According to at least one embodiment, the execution of the start sequence comprises switching the radiation emitting unit from the low-intensity mode into the no-intensity mode if the distance of the radiation emitting unit to the irradiation object leaves the irradiation range (step S5). This may interrupt or cancel the start sequence. This step may happen automatically.

According to at least one embodiment, the execution of the start sequence comprises switching the radiation emitting unit into the nominal-intensity mode when the position of the irradiation object relative to the illumination device is adjusted such that the desired illuminated area of the irradiation object is illuminated (step S6).

According to at least one embodiment, the steps S1 to S6 are executed in the specified order and/or one after the other.

Particularly before starting the actual illumination session, it may be desired to correctly position the irradiation object with respect to the illumination device or vice versa. When the radiation emitting unit is switched on, the distance sensor is activated so that the distance to the irradiation object is measured. The radiation emitting unit may immediately be switched into the no-intensity mode or the low-intensity mode, depending on whether the distance is outside the irradiation range or within the irradiation range. Using the low-intensity mode when the irradiation object has the correct distance to the radiation emitting unit can be used for further positioning the irradiation object relative to the illumination device. The operator may see by eye the irradiance of the irradiation object in an illuminated area caused by the radiation emitting unit in the low-intensity mode and this may help to correctly position the irradiation object relative to the illumination device or vice versa. The occurrence of pain may be prevented in the low-intensity mode due to the low intensity so that the adjustment of the position is not painful for the patient.

If two or more radiation emitting units are used, several or all radiation emitting units may be switched on in step S1, e.g. simultaneously or individually one after the other. For example, only the radiation emitting units which have been selected by an operator before (e.g. in a step S0) are switched on. If the distance of at least one radiation emitting unit to the irradiation object is not within the irradiation range or leaves the irradiation range, only this radiation emitting unit or several radiation emitting units or all radiation emitting units may be switched into the no-intensity mode. This may happen automatically. Furthermore, if at least one radiation emitting unit is not in the low-intensity mode and/or the distance of at least one radiation emitting unit to the irradiation object is not in the irradiation range, none of the radiation emitting units may be switchable into the nominal-intensity mode.

Alternatively, all radiation emitting units may be switchable into the nominal-intensity mode regardless of whether one or more or all radiation emitting units are in the low-intensity mode or whether the distances are in the irradiation range. Alternatively, only those radiation emitting units for which the respective distance is not in the irradiation range and/or which are not in the low-intensity mode may be prevented from being switched into the nominal intensity mode.

Hereinafter, an illumination device and a method for treating a skin disease described herein will be explained in more detail with reference to drawings on the basis of exemplary embodiments. Same reference signs indicate same elements in the individual figures. However, the size ratios involved are not necessarily to scale, individual elements may rather be illustrated with an exaggerated size for a better understanding.

Next, a method for operating an illumination device is specified. Particularly, an illumination device specified herein can be operated with this method. All features disclosed in connection with the illumination device are therefore also disclosed for the method and vice versa.

According to at least one embodiment, the method comprises a step in which a measurement signal is provided, said measurement signal being indicative for a distance between the radiation emitting unit and the irradiation object. In a further step, an operation signal is generated as a function, i.e. depending on, of the measurement signal, said operation signal being configured to cause the illumination device to adjust the operation of the illumination device or to call or to trigger a call for an adjustment of the operation of the illumination device.

Furthermore, a computer program product is specified. The computer program product comprises machine-readable instructions, which, when loaded and executed on a processor, are configured to cause the illumination device to execute the method for operating the illumination device. The processor may be part of the illumination device.

Moreover, a computer-readable medium is specified, having stored thereon the computer program product.

DETAILED DESCRIPTION OF THE INVENTION

Figure 1:
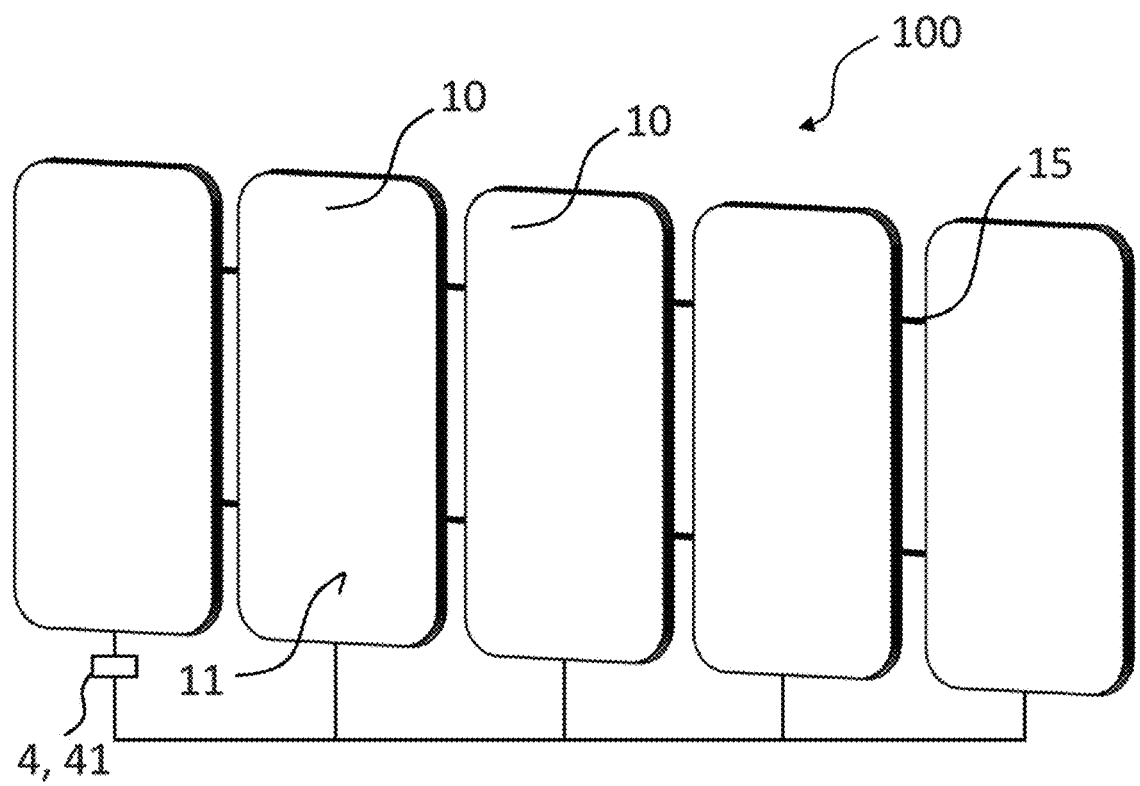
FIGS. 1 and 2 show an exemplary embodiment of the illumination device in different configurations.

FIG. 1 shows an exemplary embodiment of the illumination device 100 for photodynamic therapy. The illumination device 100 comprises several radiation emitting units 10 which are linearly connected to each other. The radiation emitting units 10 are movably, especially pivotally, connected to each other. For this purpose, hinges 15 are used between the radiation emitting units 10. The radiation emitting units 10 each comprise a radiation output area 11 through which radiation generated by the respective radiation emitting unit 10 is coupled out of the illumination device 100. The output areas 11 are, for example, in each case formed by a (plexiglass or glass) cover plate of the respective radiation emitting unit 10.

In FIG. 1, the illumination device 100 is configured to irradiate a plane surface. The radiation emitting units 10 are arranged such that the radiation output areas 11 lie substantially in a common plane. Main radiation directions of the radiation emitting units 10 are substantially parallel to each other.

Figure 2:
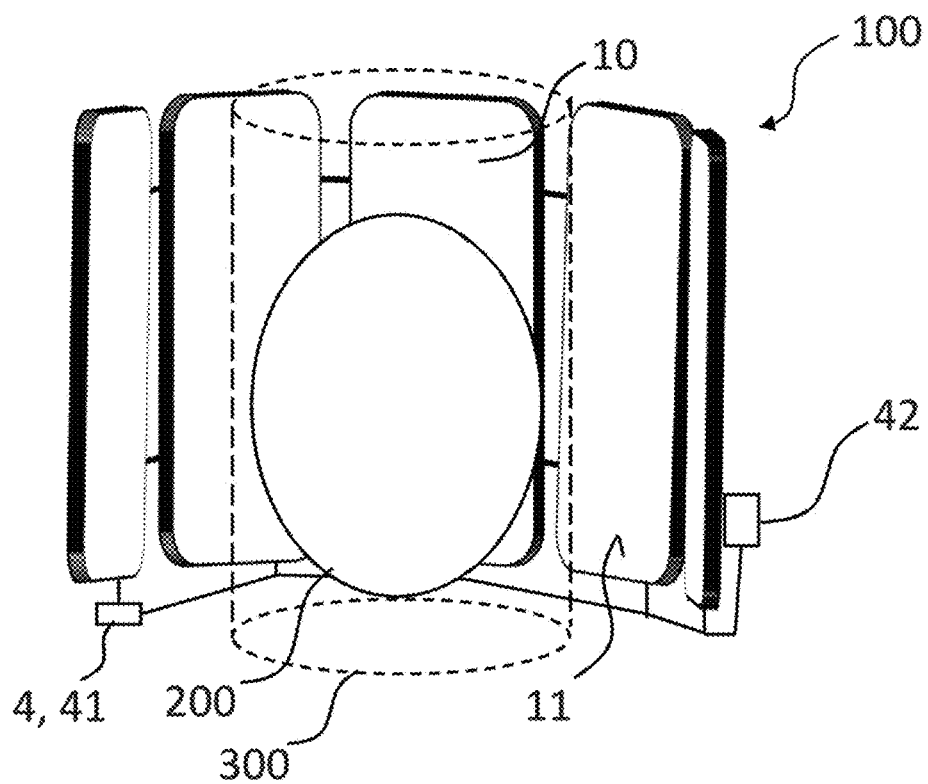

FIG. 2 shows the illumination device 100 of FIG. 1 in a different configuration in which the illumination device 100 is configured to irradiate a surface of non-plane shape, namely a cylinder surface, particularly a human face. The radiation emitting units 10 are arranged in a C-shape configuration. For this purpose, the radiation emitting units 10 have been pivoted relative to each other so that the distances of the radiation output areas 11 of the radiation emitting units 10 to the cylinder surface are substantially the same. The rearrangement or movement of the radiation emitting units 10 can be done manually. In the present case, each radiation emitting unit 10 is assigned a motor 42, which is configured to move/pivot the respective radiation emitting unit 10 relative to the further radiation emitting units 10.

The cylinder around which the radiation emitting units 10 are arranged defines a predetermined object location 300. The object location 300 is arranged at a distance to the radiation output areas 11 of the radiation emitting units 10. Inside the object location 300, an irradiation object 200 is arranged. The irradiation object 200 is, for example, a human head. The head 200 is therapeutically treated by irradiating with the irradiation device 100.

During therapeutic treatment, the distances of the radiation emitting units 10 with respect to the irradiation object 200 or with respect to the predetermined object location 300 shall be kept substantially constant, particularly at a nominal distance or within an irradiation range around the nominal distance. For this purpose, the illumination device 100 comprises a location or distance monitoring system 4. The monitoring system 4 comprises distance sensors 40 (see for example FIG. 4), each radiation emitting unit 10 assigned one distance sensor 40. The distance of the radiation emitting units 10 with respect to the irradiation object 200 or the predetermined object location 300 is measured with help of the distance sensors 40.

The monitoring system 4 further comprises an electronic control unit 41 and the motors 42 specified above. During operation of the illumination device 100, the distances of the radiation emitting units 10 to the irradiation object 200 or the predetermined object location 300 is constantly or repeatedly measured with help of the distance sensors 40. Corresponding measurement signals are processed in the monitoring system 4. In case the measurement signals indicate a variation in the distance of one radiation emitting unit 10 to the object 200 or the location 300, a corresponding operation signal or corresponding operations signals are generated, which cause the electronic control unit 41 to operate one or more motors 42 in order to adjust the distance of the radiation emitting units 10 with respect to the irradiation object 200 or the predetermined object location 300. For example, the distance is kept between 50 mm inclusive and 200 mm inclusive, preferably 125 mm. By way of example, if a variation in the distance of more than or equal to 15 mm is measured, the distance is adjusted. For operation the illumination device as stated above and in the following, the computer program product specified herein may be executed on a processor of the illumination device.

Additionally or alternatively, the monitoring system 4 may be configured to call for an adjustment, if the measurement signals form the distance sensors 40 indicate a variation in the distance and/or a leaving of the irradiation range. The operation signal(s) are then configured to call or to trigger a call for such an adjustment. An operator may then move the radiation emitting units 10 manually or by operating the motors 42.

The illumination device 100 may be further configured to adjust the radiation power emitted by the respective radiation emitting unit and/or to adjust the duration of the illumination session. The electronic control unit 41 or a different electronic control unit may then, as a function of the measurement signals of the distance sensors 40, vary the radiation power on the basis of one or more operation signals generated as a function of the measurement signals. For example, if the distance increases, the radiation power is increased. If the distance is reduced, the radiation power may be reduced. Additionally or alternatively, if the distance increases, the duration of the illumination session may be increased and if the distance decreases, the duration of the illumination session may be reduced. Increasing or reducing the duration of the illumination session may be controlled automatically by the monitoring system 4. Particularly, the monitoring system 4 ensures that the predetermined light dose, of e.g. 37 J/cm$^2$, is received.

Figure 12:
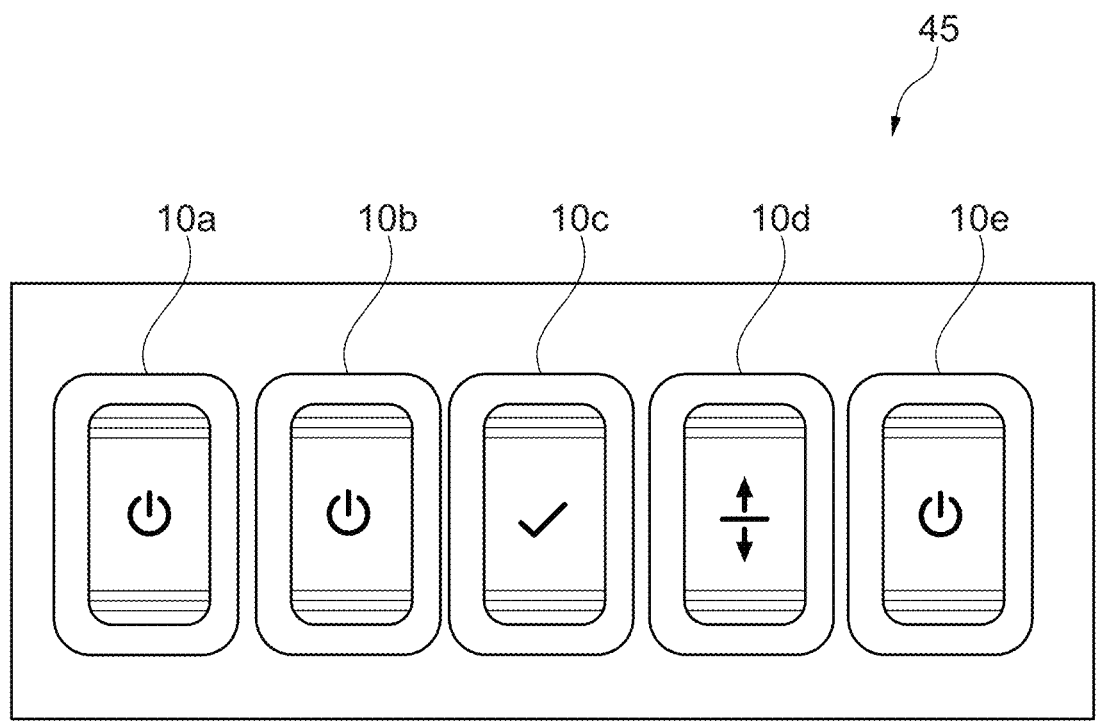
FIG. 12 shows an exemplary embodiment of a graphical user interface of a feedback system.

It is also possible that, as a function of the measurement signals of the distance sensors 40, the monitoring system 4 may call for an adjustment of the radiation power or the duration of the illumination session, e.g. by an according output on a display or a different user interface of the system (see FIG. 12, for example). An operator may then vary the radiation power of the respective radiation emitting unit 10 or may increase or reduce the duration of the illumination session.

The illumination device 100 may further comprise a feedback system (see FIG. 12) which is configured to provide feedback in order to assist in keeping the irradiation object 200 at the predetermined object location 300. The feedback system may be configured to issue visual, audible and/or tactile feedback which indicates whether the object 200 is at the predetermined object location 300 or at a distance to the radiation emitting units 10 within the irradiation range, respectively, or if an adjustment is required. For this purpose, the feedback system may comprise a display and/or a loudspeaker.

FIG. 12 shows an exemplary embodiment of a graphical user interface 45 of such a feedback system. The user interface 45 illustrates the five radiation emitting units 10*a* . . . 10*e*. Three of the radiation emitting units 10*a*, 10*b*, 10*e* are indicated to be not activated/switched on, which is indicated by the "off"-symbols in the respective radiation emitting unit. One radiation emitting unit 10*c* is activated/switched on and at the correct distance (within the irradiation range), indicated by the check mark in that radiation emitting unit. One radiation emitting unit 10*d* is activated/switched on but an adjustment of the distance is called for or is being carried out by the monitoring system itself. This is indicated by the two arrows pointing in opposite directions. The representation on the user interface 45 might be generated by the computer program product specified herein.

Before starting an illumination session with the illumination device 100, a start sequence may be performed. Firstly, the operator may switch on each of the radiation emitting units, e.g. by operating one or more buttons on the user interface 45. By switching on, the distance sensors 40 may be activated. After switching on, the radiation emitting units 10 may first be in a no-intensity mode, in which no radiation is emitted, or may be in a low-intensity mode, in which a low radiation intensity is emitted. The operator may then adjust the distances between the radiation emitting units 10 and the irradiation object 200 in order to have the distance of each radiation emitting unit 10 to the irradiation object 200 in the irradiation range, which is, e.g., between 11 cm and 14 cm. The user interface 45 might indicate for each radiation emitting unit 10 the distance to the irradiation object 200 and/or if the distance has to be increased or reduced in order to come into the irradiation range.

As soon as the distance of a radiation emitting unit 10 to the irradiation object 200 is within the irradiation range, a check mark may appear on the user interface 45 for the respective radiation emitting unit 10 (see FIG. 12). The radiation emitting unit 10 in the correct distance, namely in the irradiation range, may then be automatically switched from the no-intensity mode into the low-intensity mode. A corresponding illumination caused by said radiation emitting unit may be visible on the irradiation object 200.

When all radiation emitting units 10 are in the correct distance to the irradiation object 200, particularly when check marks appear on the interface 45 for all radiation emitting units 10, all radiation emitting units 10 may be in the low-intensity mode. The operator may now further adjust the position of the illumination device 100 relative to the irradiation object 200, for example by shifting the illumination device 100 from a position illuminating an upper head region into a position in which the illumination device 100 illuminates the lower head region. During this adjustment of the position, the distances shall be maintained within the irradiation ranges. If, however, during said adjustment of the position the distance of one of the radiation emitting unit 10 leaves the irradiation range, this radiation emitting unit 10 may be automatically switched from the low-intensity mode into the no-intensity mode. The operator may notice this by a change of the illumination on the irradiation object 200. Additionally or alternatively, the interface 45 may indicate this event by letting the checkmark disappear and/or by creating a noise, for example a warning noise. The operator may then readjust the distance of this radiation emitting unit 10.

After the illumination device 100 has been brought into the correct position relative to the irradiation object 200 and when the distances of all radiation emitting units 10 are still in the irradiation range, the operator may switch one or more or all of the radiation emitting units 10 into the nominal-intensity mode, in which the radiation emitting units 10 emit the nominal radiation intensity for the treatment of the skin disease. For example, if the distance of one of the radiation emitting units 10 is not within the irradiation range, only this radiation emitting unit 10 may not be switchable into the nominal-intensity mode. It is also possible that, if at least one of the radiation emitting units 10 is not within the irradiation range, none of the radiation emitting units 10 can be switched into the nominal intensity mode. Alternatively, all radiation emitting units may be switchable into the nominal-intensity mode, regardless whether one or more or all radiation emitting units are within the irradiation range or not. Switching into the nominal-intensity mode may be done manually by the operator, e.g. by operating a start button on the interface.

Figure 3:
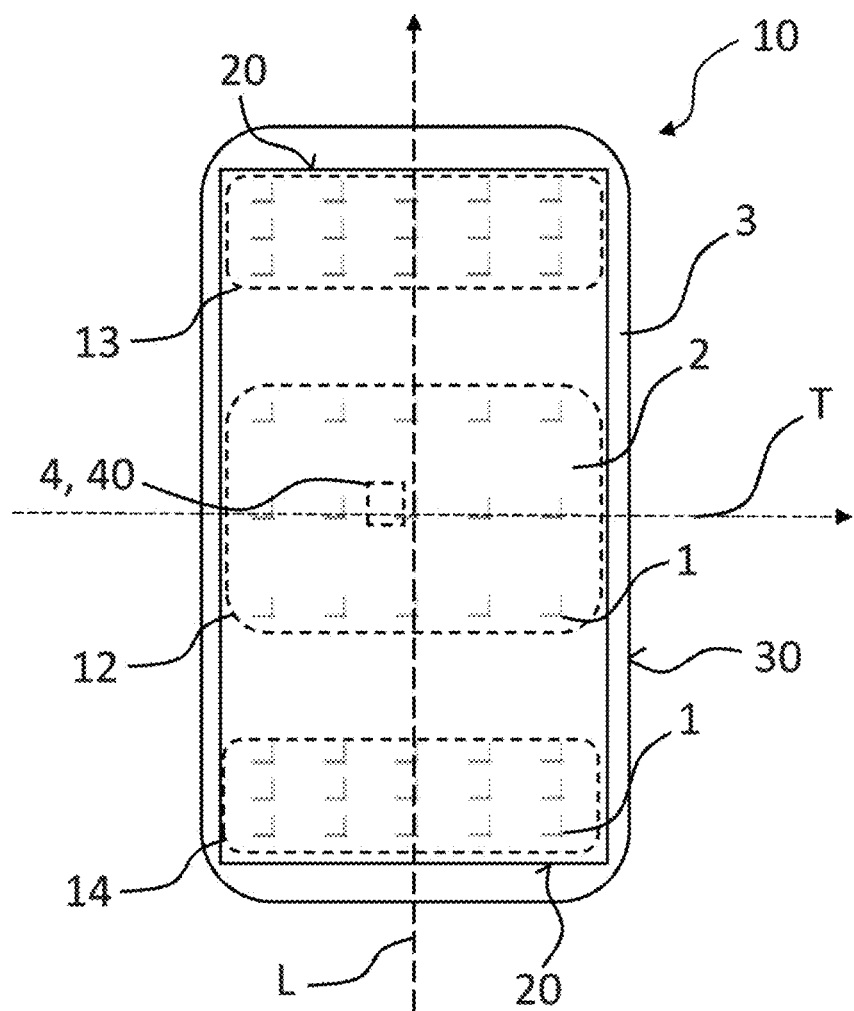
FIGS. 3 to 8 show exemplary embodiments of radiation emitting units.

FIG. 3 shows an exemplary embodiment of a radiation emitting unit 10 in plan view of the radiation emitting unit 10, for example in plan view of the cover plate. The radiation emitting unit 10 of FIG. 3 is, for example, used for all radiation emitting units 10 in the illumination device 100 of FIGS. 1 and 2.

The radiation emitting unit 10 comprises a unit housing 3, for example comprising metal and/or plastic, and a radiation source carrier 2 laterally surrounded by the unit housing 3 in the shown plan view. The unit housing 3 defines a lateral edge 30 of the radiation emitting unit 10 delimiting the radiation emitting unit 10 in a transversal direction T.

The radiation source carrier 2 is, for example, a printed circuit board, PCB for short. The radiation source carrier 2 is an elongated, rectangular shaped carrier. A main direction of extension of the radiation source carrier 2 defines a longitudinal direction L. A direction perpendicular to the longitudinal direction L and running parallel to a main extension plane of the radiation source carrier 2 defines the transversal direction T. The radiation source carrier 2 is delimited in the longitudinal direction L and in the transverse direction T by carrier edges 20.

A plurality of radiation sources 1 is arranged on the radiation source carrier 2. The exact positions of the radiation sources 1 on the radiation source carrier 2 is indicted by the intersection points of the squared brackets. For example, a center of a chip surface of a semiconductor chip assigned to the radiation source overlaps with the respective intersection point.

In the exemplary embodiment, all radiation sources 1 of the radiation emitting unit 10 are arranged on a common radiation source carrier 2. During intended operation, all radiation sources 1 preferably emit radiation in the visible spectrum and of essentially the same color and/or with essentially the same peak wavelength.

As can be seen in FIG. 3, the radiation sources 1 are arranged on the carrier 2 in three different groups 12, 13, 14, wherein each radiation source 1 is uniquely assigned to one group 12, 13, 14. The groups 12, 13, 14 are indicated by the dashed rectangles. A first group 12 with 15 radiation sources 1 is located in a center region of the radiation source carrier 2. A second 13 and a third 14 group, each with 15 radiation sources 1, are located on peripheral regions of the radiation source carrier 2. When viewed along the longitudinal direction L, the second 13 and third 14 group are located before and behind the first group 12. Within each group 12, 13, 14 the radiation sources 1 are arranged in a two-dimension regular group pattern. The group patterns of the second 13 and third 14 group are identical, whereas the group pattern of the first group 12 is different.

In the second 13 and the third 14 group, the radiation sources 1 are arranged more densely on the radiation source carrier 2 than in the first group 12. Thus, the occupancy density of the radiation source carrier 2 with radiation sources 1 in the second 13 and third 14 group is greater than in the first group 12. This arrangement is particular advantageous in terms of a homogeneous irradiation of the irradiation object along the longitudinal direction L.

As can also be seen in FIG. 3, the distance between two adjacent groups 12, 13, 14 is greater than a distance between the radiation sources 1 within a group 12, 13, 14 (the distance between two adjacent groups is the shortest distance between two radiation sources 1 of these two groups). Moreover, it is visible form FIG. 3 that the two-dimensional pattern in which the radiation sources 1 are arranged on the radiation source carrier 2 is symmetric with respect to an axis running parallel to the longitudinal direction L and also with respect to an axis running parallel to the transversal direction T.

In the exemplary embodiment of FIG. 3, a radiation source 1 is arranged in the geometric center of the radiation source carrier 2. Slightly offset from this geometric center, a distance sensor 40 is arrange on the radiation source carrier 2. The distance sensor 40 is part of the previously described monitoring system 4. The distance sensor 40 is, for example, a time-of-flight sensor comprising a laser diode. A distance to the adjacent radiation source 1 in the geometric center is, e.g., 10 mm.

Additionally or alternatively, the distance sensor 40 may be slightly offset, e.g. by at least 5 mm and at most 40 mm, form the center of a radiation field created by the radiation sources of the radiation emitting unit. The center of the radiation field may be the position of the center of mass when integrating over all the radiation sources of the radiation emitting unit.

Figure 4:
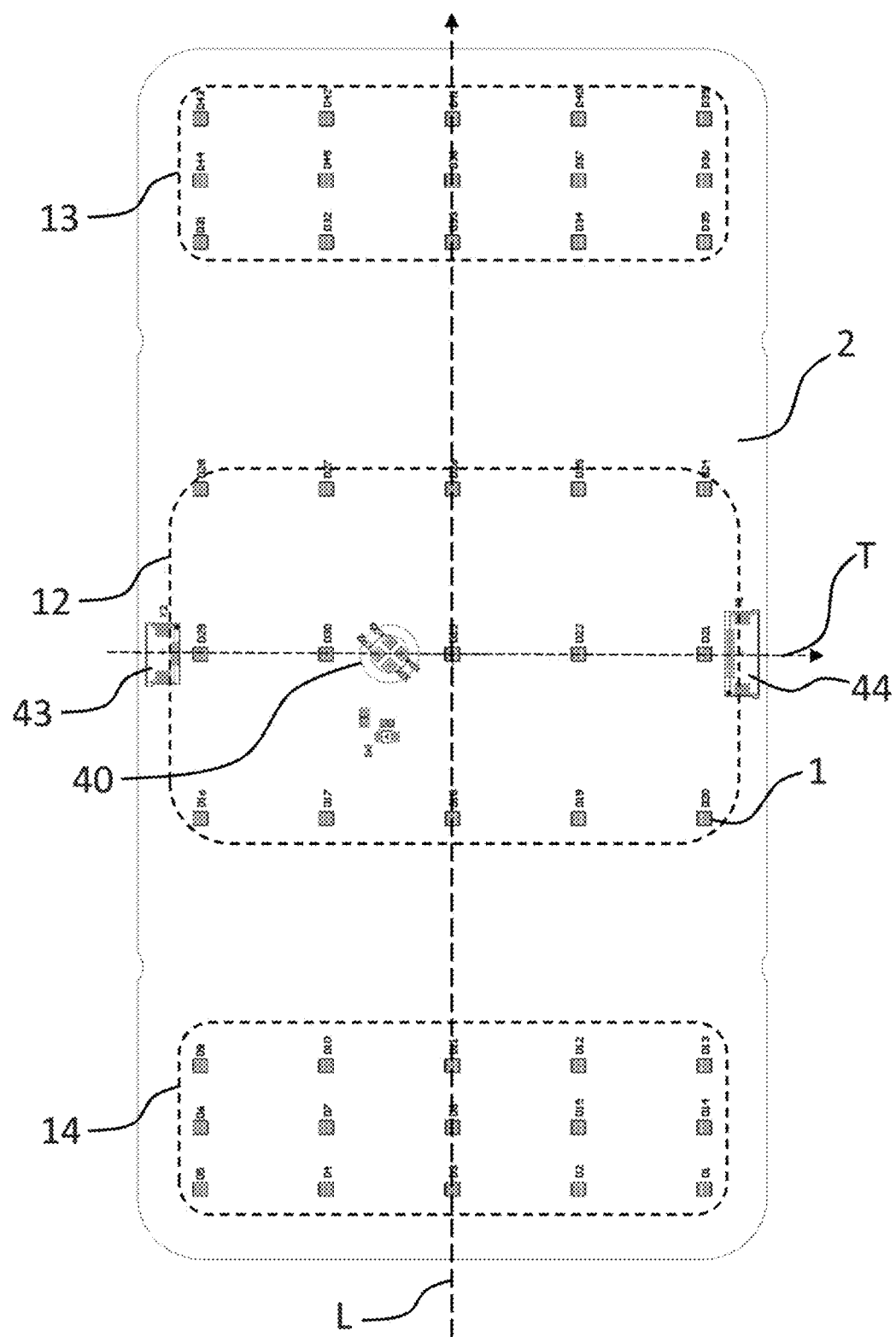

FIG. 4 shows an exemplary embodiment of a radiation emitting unit 10 in a true-to-scale view. This exemplary embodiment might be used in the illumination device 100 of FIGS. 1 and 2. The transversal distance between two radiation sources 1 being adjacent along the transversal direction T is 30 mm in each case. The longitudinal distance between two radiation sources 1 being adjacent along the longitudinal direction L is 15 mm in the second 13 and third 14 group and is 40 mm in the first group 12. The longitudinal distance between two adjacent groups is 60 mm. The radiation source carrier 2 may have an expansion along the transversal direction T of 160 mm and along the longitudinal direction of 280 mm. Connectors 43, 44 for a connection to other radiation emitting units are provided.

Figure 5:
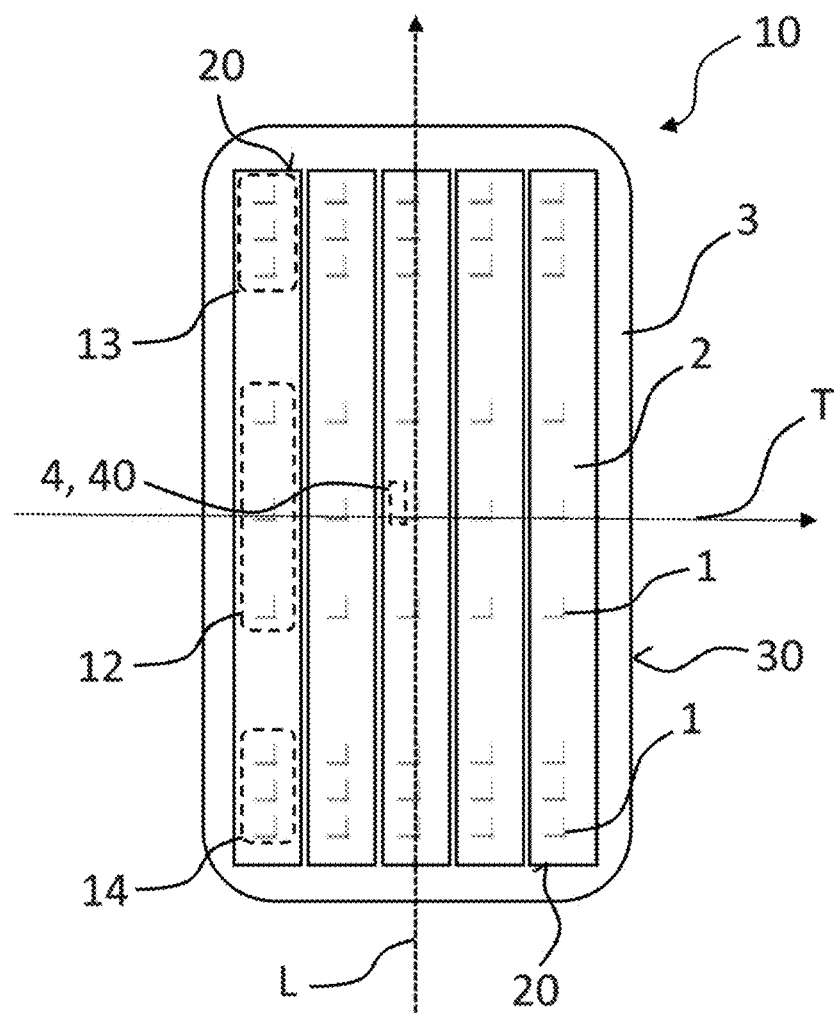

FIG. 5 shows a further exemplary embodiment of a radiation emitting unit 10 in plan view. Also this radiation emitting unit 10 might be used for the radiation emitting units 10 in the illumination device 100 of FIGS. 1 and 2. In contrast to FIGS. 3 and 4, the radiation emitting unit 10 of FIG. 5 does not only comprise one radiation source carrier 2 common to all radiation sources 1 of the respective radiation emitting unit 10, but several radiation source carriers 2. Each radiation source carrier 2 is elongated with a main direction of extension parallel to the longitudinal direction L. Along the transversal direction T running perpendicularly to the main longitudinal direction L, the radiation source carriers 2 are arranged one behind the other.

On each radiation source carrier 2, a plurality of radiation sources 1 is arranged. The radiation sources 1 are in each case arranged in a one-dimensional irregular pattern. Again, on each radiation source carrier 2, the radiation sources 1 are grouped in three groups 12, 13, 14. Each group 12, 13, 14 comprises three radiation sources 1. The first group 12, located in each case between the second 13 and the third 14 group, has a smaller occupancy density with radiation sources 1 than the respective second 13 and third 14 group. The group pattern in each group 12, 13, 14 is regular.

Figure 6:
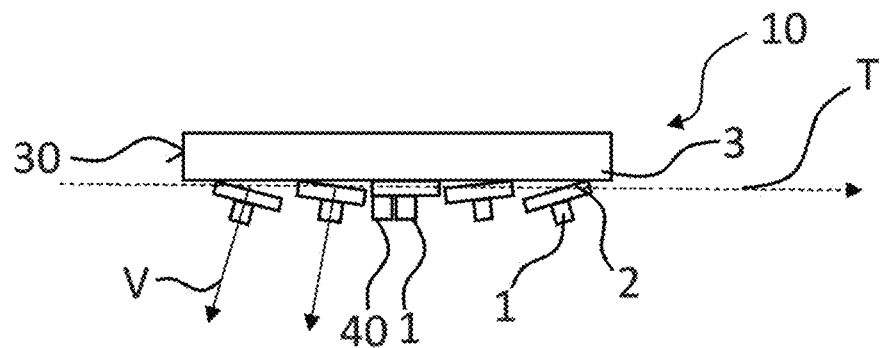

Using several radiation source carriers 2 can be advantageous for further improving the homogeneity of the irradiation pattern. As shown in FIG. 6, which is a cross sectional view along the transversal direction T of FIG. 5, the individual radiation source carriers 2 are arranged angled relative to one another. Consequently, the main radiation directions V of the radiation sources 1 of different radiation source carriers 2 are tilted relative to each other. In the exemplary embodiment of FIG. 6, the radiation source carrier 2 closets to the outer edges 30 of the housing unit 3 is oriented such that the main radiation direction V of the respective radiation sources 1 on this radiation source carrier 2 is outwardly offset from a main radiation direction V of the radiation sources 1 on another radiation source carrier 2 further away from the outer edge 30. In this way irradiation at the outer edges 30 of the radiation emitting unit 10 where the hinges 15 are placed (see FIGS. 1 and 2) can be improved.

The individual radiation source carriers 2 of the radiation emitting unit 10 may be fixed in their relative position to one another. Alternatively, they may be movable relative to another, for example manually or with help of actuators.

Figure 7:
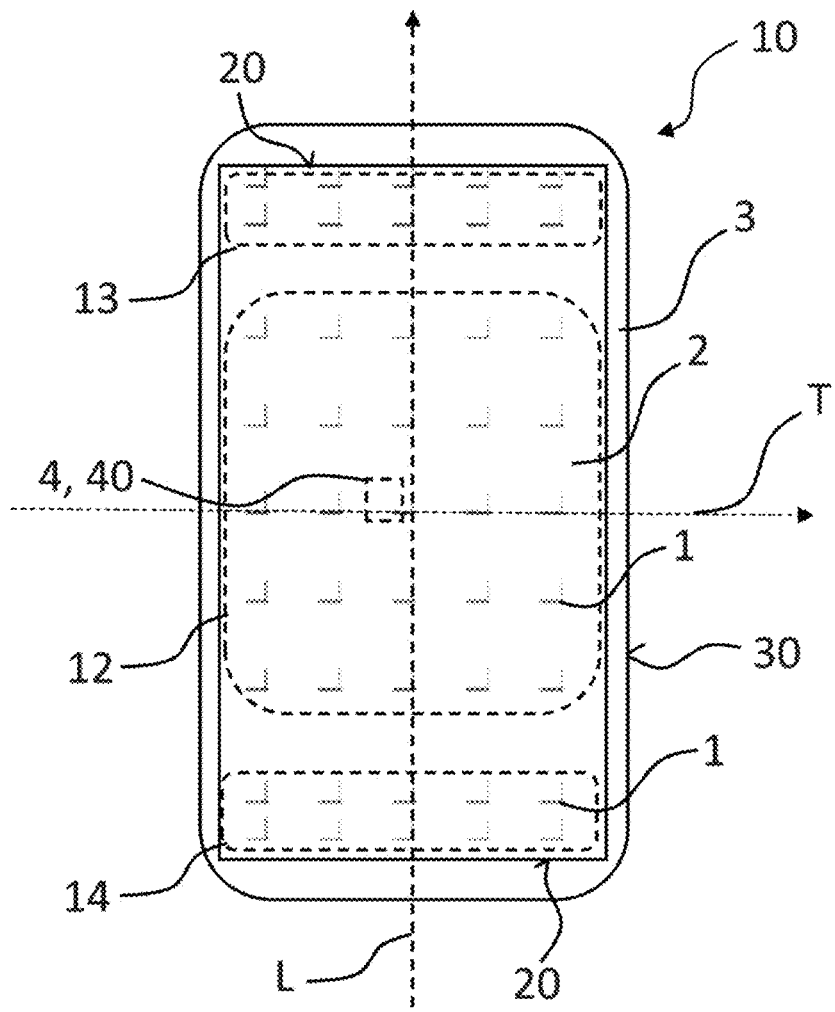

FIG. 7 shows a further exemplary embodiment of a radiation emitting unit 10 in plan view. This exemplary embodiment is similar to the ones of FIGS. 3 and 4. Again, all radiation sources 1 are placed on a common radiation source carrier 2. Also this radiation emitting unit 10 may be used for the radiation emitting units 10 in the illumination device 100 of FIGS. 1 and 2.

A difference of FIG. 7 to FIGS. 3 and 4 is the arrangement of the radiation sources 1 on the radiation source carrier 2. In FIG. 7, the first group 12 comprises 25 radiation sources 1 arranged in a regular group pattern. The second 13 and third 14 group each comprise only ten radiation sources 1 in each case arranged in a regular group pattern. In the first group 12, the transversal distances between adjacent radiation sources 1 is in each case 30 mm and the longitudinal distance between adjacent radiation sources 1 is in each case 35 mm. In the second 13 and third 14 group, the transversal distance between adjacent radiation sources 1 is in each case 30 mm and the longitudinal distance is in each case 15 mm. The longitudinal distance between two adjacent groups 12, 13, 14 is 45 mm in each case.

Figure 8:
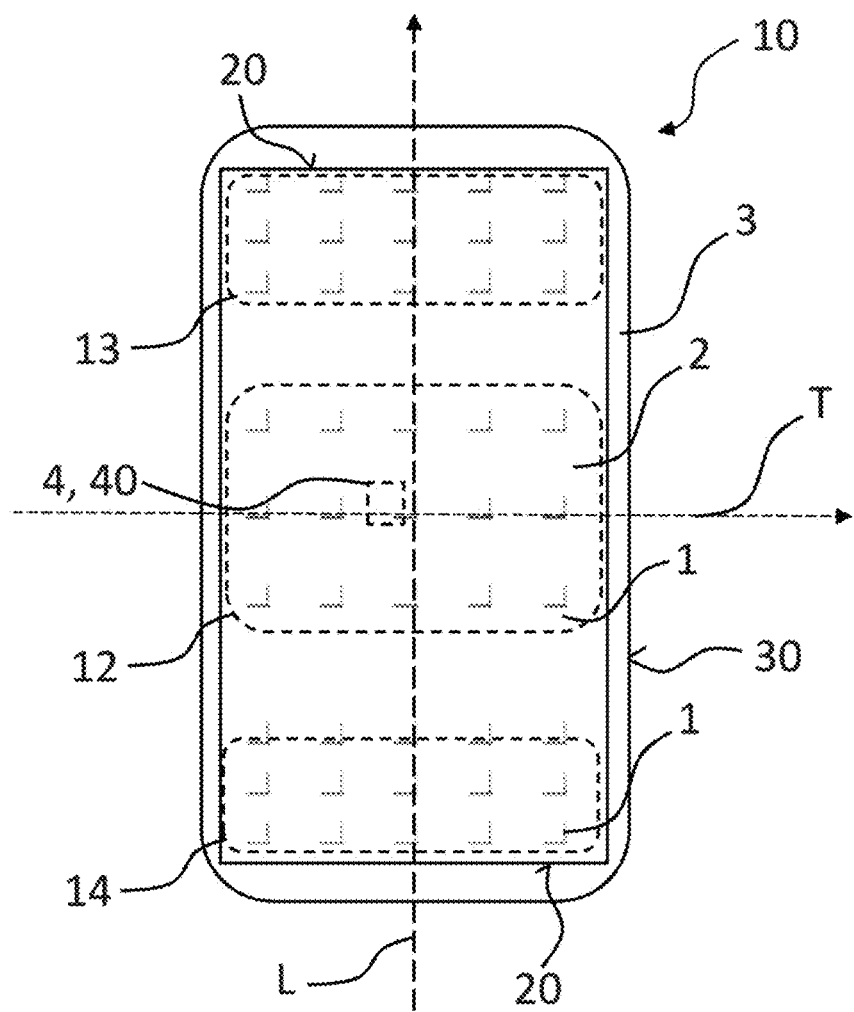

FIG. 8 shows an exemplary embodiment of a radiation emitting unit 10, for which a particularly homogeneous irradiation pattern along the longitudinal direction could be obtained. The arrangement of the radiation sources 1 on the radiation source carrier 2 is similar to FIG. 3 or FIG. 4, respectively. Only the longitudinal distances are chosen slightly differently. In the first group 12, the longitudinal distances between adjacent radiation sources 1 is 36 mm in each case. In the second 13 and third 14 group, the longitudinal distances between adjacent radiation sources 1 are 22 mm in each case. The longitudinal distance between adjacent groups 12, 13, 14 is 28 mm in each case.

Figure 9:
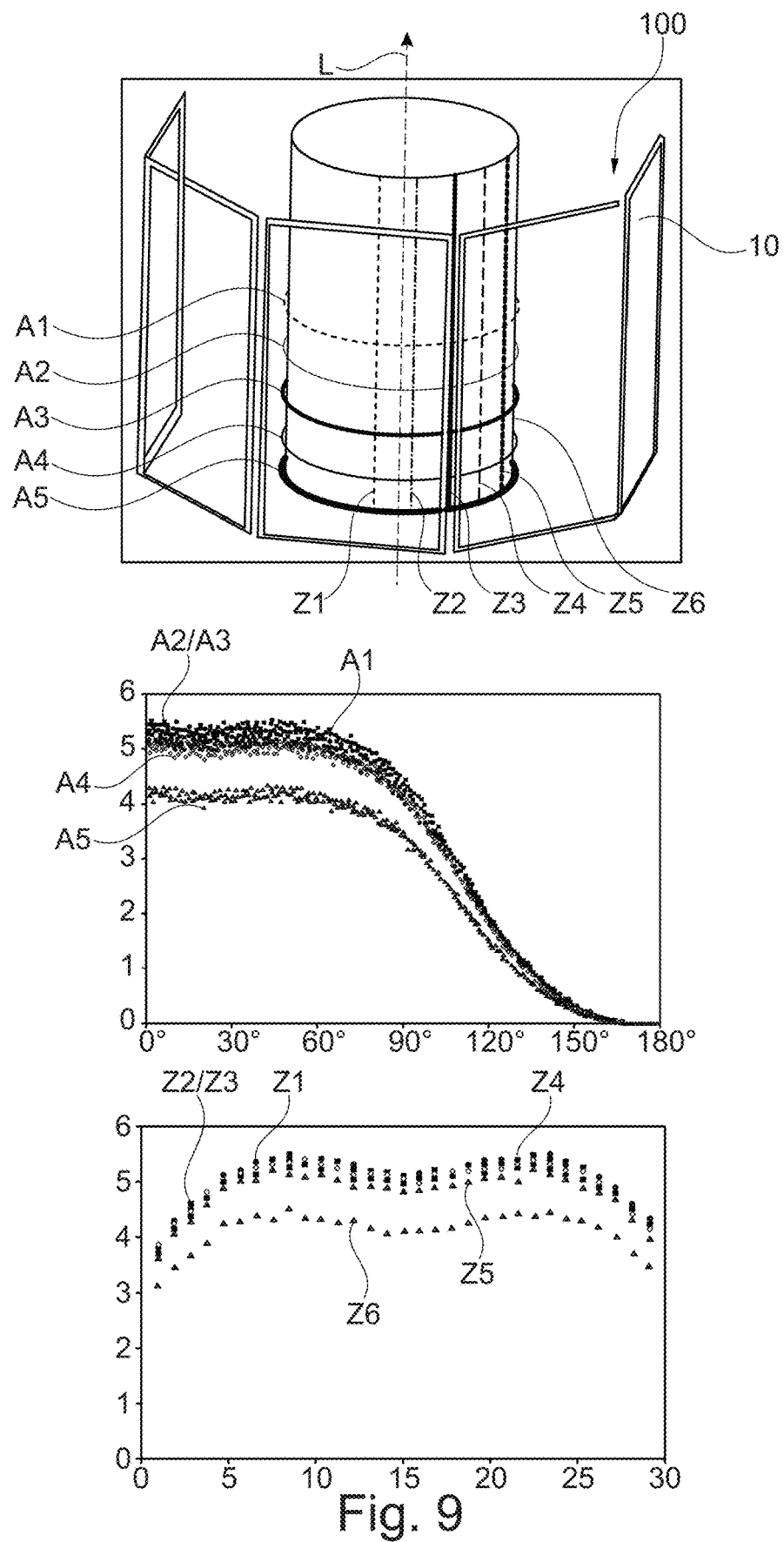
FIG. 9 shows simulation results for the irradiance on a cylindrical surface obtained with an exemplary embodiment of the illumination device.

FIG. 9 shows simulation results for the irradiance on a cylindrical surface obtained with an exemplary embodiment of the illumination device 100. For this simulation, an illumination device 100 with five radiation emitting units 10 as described in connection with FIG. 3 was used. The radiation emitting units 10 were arranged around a cylinder with a diameter of 200 mm and a height of 300 mm. The radiation emitting units 10 were arranged such that the distance of the radiation output area 11 of each radiation emitting unit 10 to the cylinder surface was 125 mm. The upper picture of FIG. 9 shows the arrangement.

The homogeneity of the irradiance on the cylinder surface was investigated as a function of the azimuthal angle (middle picture of FIG. 9). On the y-axis, the irradiance in arbitrary units is shown. On the x-axis the azimuthal angle is shown. The different data samples Z1 . . . Z5 correspond to measurements at different heights along the longitudinal direction L (see also upper picture of FIG. 9).

In the lower picture of FIG. 9, the irradiance in arbitrary units (y-axis) is shown as function of the height along the longitudinal direction L (x-axis). The different data samples Z1 . . . Z6 correspond to measurements at different azimuthal angles.

As becomes clear from FIG. 9, lower picture, the special arrangement of the radiation sources 1 on the respective radiation source carriers 2 of the radiation emitting units 10 results in a very homogeneous irradiance along the longitudinal direction L.

In FIG. 9, middle picture, one can see that due to the configuration of the illumination device 100 with several radiation emitting units 10, which are pivotally connected to each other, and thus can be arranged around the cylinder with equal distances to the cylinder surface, a very homogenous irradiance along the azimuthal angle up to 90° is obtained.

Figure 10:
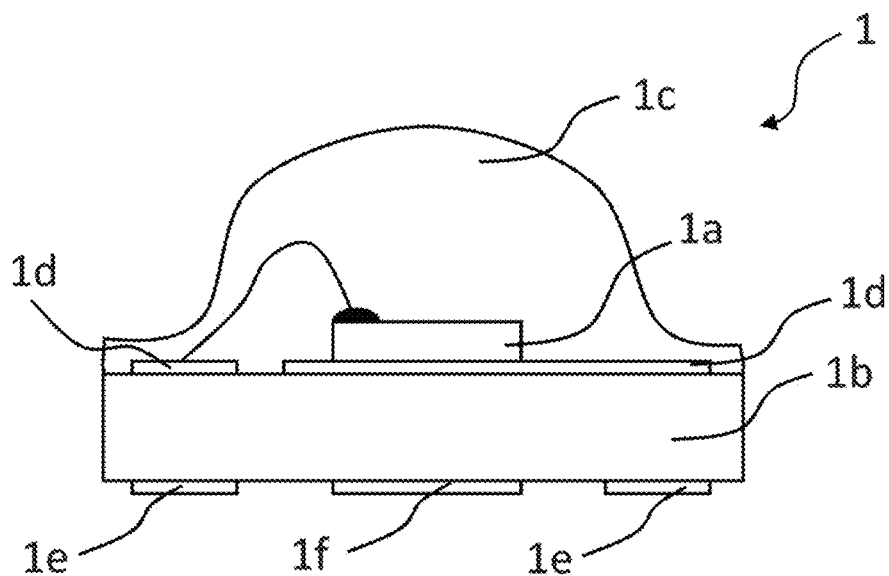
FIG. 10 shows an exemplary embodiment of a radiation source.

FIG. 10 shows an exemplary embodiment of a radiation source 1 being an optoelectronic component. All radiation sources 1 of the radiation emitting unit 10 or of the whole illumination device 100 are preferably formed identically within the manufacturing tolerance and may each be such an optoelectronic component.

The optoelectronic component 1 comprises a semiconductor chip 1a, for example based on a III-V-compound semiconductor material. The semiconductor chip 1a is mounted on a front side of a ceramic chip carrier 1b. The chip carrier 1b may be pierced by through connections (not shown), electrically connecting metallic front side pads 1d on the front side with metallic rear side pads 1e on the rear side of the chip carrier 1b. The semiconductor chip 1a is electrically connected to the front side pads 1d. A thermal pad 1f, for example made of metal, on the rear side helps to remove heat from the optoelectronic component 1.

The semiconductor chip 1a is embedded in a lens-shaped encapsulation 1c, which collimates the radiation coming from the semiconductor chip 1a. The encapsulation is, for example, made of transparent silicone.

The properties of the optoelectronic component 1 are, for example, as follows: A peak wavelength of the emitted radiation is 634.0 nm when operated with an operation current of 350 mA and at an operation temperature of 25° C. An opening angle into which at least 75% of the radiation intensity is emitted is at most 80°. A main radiation direction is 0°, wherein the radiation direction is measured relative to a normal axis running perpendicularly to a main extension plane of the chip carrier 1b or to a radiation exit surface of the semiconductor chip 1a. The emission angle at which the radiance decreases from its maximum at 0° to 50% of the maximum value is at ±40°. The luminous efficacy is 111 lm/W.

During operation of the illumination device 100, each optoelectronic component 1 is, for example, operated with an operation current of 1000 mA.

Figure 11:
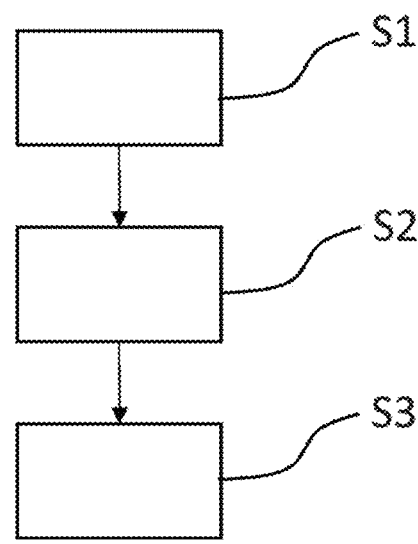
FIG. 11 shows an exemplary embodiment of the method for treating a skin disease on the basis of a flow chart.

FIG. 11 shows an exemplary embodiment of the method for treating a skin disease on the basis of a flow chart. In a step S1, a pharmaceutical substance is applied to the surface of the skin of a human being in a region which is to be treated. It might be the region in a face. The pharmaceutical substance is, for example, a photosensitizing drug or precursor to such a drug that is excitable by light in the radiation spectrum emitted by the illumination device 100. The pharmaceutical substance may comprise 5-aminolevulinic acid.

In a step S2, the skin region to be treated is arranged in the predetermined object location 300 of the illumination device 100 (see FIG. 2).

In a step S3, the skin region to be treated is irradiated with the illumination device, for example for at least 10 min and at most 20 min. During the illumination session, the skin region is irradiated with a predetermined light dose of, e.g., at least 30 and at most 45 J/cm$^2$, such as 37 J/cm$^2$. A light dose of 37 J/cm$^2$ is especially suitable if red light with a wavelength of about 635 nm is used to irradiate the object. In case green or blue light is used, e.g. for irradiating a skin surface onto which ALA has been topically applied before the irradiation, the total light dose applied to the irradiation object during the illumination session may have a different value due to the different absorption properties for these wavelengths. The general teaching in the present disclosure does not only apply for light sources emitting red light but also for light sources of different colored light, e.g. blue or green light, particularly if ALA-based PDT is performed.

The invention described herein is not limited by the description in conjunction with the exemplary embodiments. Rather, the invention comprises any new feature as well as any combination of features, particularly including any combination of features in the patent claims, even if said feature or said combination per se is not explicitly stated in the patent claims or exemplary embodiments.

In the following, a set of embodiments is disclosed. The embodiments are numbered to facilitate referencing the features of one embodiment in other embodiments. The embodiments form part of the disclosure of the present application and could be made subject to independent and/or dependent claims irrespective of what currently is claimed in the application and also independent of the references in brackets. We note, however, that the scope of protection is defined by the appended claims, where the following embodiments do not constitute claims. The embodiments are:

Embodiments

1. Illumination device (100) for photodynamic therapy,
the illumination device (100) comprising at least one electromagnetic radiation emitting unit (10),
the at least one electromagnetic radiation emitting unit (10) comprising at least one electromagnetic radiation source (1),
the electromagnetic radiation source (1) being configured to generate radiation for the irradiation of a region of an irradiation object (200) in an illumination session,
wherein the irradiation object (200) is to be arranged at a predetermined object location (300),
wherein the predetermined object location (300) is arranged at a distance relative to a radiation output area (11) of the radiation emitting unit (10) through which the radiation generated by the at least one electromagnetic radiation source (1) exits the radiation emitting unit (10) during operation of the illumination device (100).

2. Illumination device (100) according to embodiment 1,
wherein the radiation emitting unit (10) comprises a plurality of radiation sources (1) arranged on a common radiation source carrier (2),
wherein an occupancy density of the radiation source carrier (2) with radiation sources (1) is smaller in a center region of the radiation source carrier (2) than in peripheral regions of the radiation source carrier (2) outside the center region.

3. Illumination device (100) according to embodiment 2, wherein the radiation sources (1) are arranged in a one- or two-dimensional pattern on the radiation source carrier (2).

4. Illumination device (100) according to embodiment 3, wherein the pattern is irregular.

5. Illumination device (100) according to any of the embodiments 2 to 4,
wherein the radiation source carrier (2) is an elongate carrier with a main direction of extension defining a longitudinal direction (L).

6. Illumination device (100) according to embodiment 3 or any of embodiments 4 and 5 in their dependency of embodiment 3,
wherein the pattern is symmetrical relative to one axis or two axis, which are perpendicular.

7. Illumination device (100) according to any of the embodiments 2 to 6,
wherein the radiation sources (1) on the radiation source carrier (2) are grouped into a plurality of groups (12, 13, 14), wherein the radiation sources (1) of each group (12, 13, 14) are arranged in a regular group pattern, wherein at least two groups (12, 13) of the plurality of groups have different group patterns.

8. Illumination device (100) according to embodiment 7,
wherein at least two groups (13, 14) of the plurality of groups (12, 13, 14) have the same group pattern.

9. Illumination device (100) according to embodiment 8,
wherein a first group (12) with a first group pattern is arranged between a second group (13) and a third group (14), when seen in plan view of the radiation source carrier (2),
wherein the second (13) and the third (14) group have the same group pattern and the first group (12) has a different group pattern.

10. Illumination device (100) according to any of the preceding embodiments, wherein the radiation emitting unit (10) comprises a unit housing (3) which defines an outer edge (30) of the radiation emitting unit (10).

11. Illumination device (100) according to embodiment 10,
wherein the radiation emitting unit (10) comprises a plurality of radiation source carriers (2), each radiation source carrier (2) being provided with a plurality of radiation sources (1),
wherein the radiation source carrier (2) closest to the outer edge (30) is oriented such that a main radiation direction (V) of the radiation sources (1) on this radiation source carrier (2) is outwardly offset from a main radiation direction (V) of the radiation sources (1) on another radiation source carrier (2) further away from the outer edge (30).

12. Illumination device according to any of the preceding embodiments,
wherein the radiation emitting unit (10) comprises one continuous radiation source carrier (2) common for all radiation sources (1) of the radiation emitting unit (10).

13. Illumination device according to any of the embodiments 1 to 10,
wherein the radiation emitting unit (10) comprises a plurality of radiation source carriers (2), each radiation source carrier (2) being provided with a plurality of radiation sources (1), at least two radiation source carriers (2) being arranged angled relative to one another, wherein the radiation source carriers (2) are
  fixed in their relative position to one another or
  movable relative to one another.

14. Illumination device (100) according to any of the preceding embodiments,
wherein the at least one radiation source (1) is an optoelectronic component,
wherein the emission spectrum of the optoelectronic component has a peak wavelength in one of the following ranges: 635 nm±4 nm, 542 nm±4 nm, 506 nm±4 nm.

15. Illumination device (100) according to any of the preceding embodiments,
wherein the illumination device (100) comprises a plurality of radiation emitting units (10) which are movably connected to one another.

16. Illumination device (100) according to any of the preceding embodiments,
wherein the illumination device (100) comprises a location or distance monitoring system (4), wherein the monitoring system (4) is configured to monitor the location and/or the distance of the irradiation object (200) from the radiation emitting unit (10) and/or from the predetermined object location (300).

17. Illumination device (100) according to embodiment 16 in its dependency of embodiment 2, wherein
the monitoring system (4) comprises a distance sensor (40) arranged on the radiation source carrier (2) of the at least one radiation emitting unit (10),
the distance sensor (40) is located offset of a geometric center of the radiation source carrier (2) when viewed in plan view.

18. Illumination device (100) according to embodiment 17,
wherein the illumination device (100) is configured to compensate for distance or location variations of the irradiation object (200) from the respective radiation emitting unit (10) and/or the predetermined object location (300) in order to maintain a predetermined radiation dose during the illumination session.

19. Illumination device (100) according to any of embodiments 16 to 18,
wherein the monitoring system (4) is configured to adjust the operation of the illumination device (100) or to call for an adjustment of the operation of the illumination device (100) by using one of, an arbitrary combination of or all of the following measures:
varying the distance between the respective radiation emitting unit (10) and the irradiation object (200),
adjusting the radiation power emitted by the respective radiation emitting unit (10), and/or
adjusting a duration of the illumination session.

20. A method for treating a skin disease comprising the following steps:
a) applying a pharmaceutical substance to the surface of the skin in a region which is to be treated;
b) arranging the skin region to be treated in a predetermined object location (300) of the illumination device (100) according to any of the preceding embodiments,
c) irradiating the skin region to be treated with the illumination device (100).

21. A method for operating an illumination device (100) according to any of the embodiments 1 to 19, comprising the steps of:
providing a measurement signal which is indicative for a distance between the radiation emitting unit (10) and the radiation object (200),
generating an operation signal as a function of the measurement signal, said operation signal being configured to cause the illumination device (100) to adjust the operation of the illumination device (100) or to call for an adjustment of the operation of the illumination device (100).

22. Computer program product comprising machine-readable instructions, which, when loaded and executed on a processor, are configured to cause the illumination device to execute the method of embodiment 21.

23. A computer-readable medium having stored thereon the computer program product according to embodiment 22.

This patent application claims the priority of the U.S. patent application Ser. No. 17/071,496, the disclosure content of which is hereby incorporated by reference.

REFERENCE SIGN LIST

1 radiation source
2 radiation source carrier
3 unit housing
4 monitoring system
10 radiation emitting unit
10*a* . . . 10*e* graphical representations of radiation emitting units
11 radiation output area
12 first group
13 second group
14 third group
15 hinge
20 carrier edge
30 outer edge
40 distance sensor
41 electronic control unit
42 motor
43 connector
44 connector
45 graphical user interface
100 illumination device
200 irradiation object
300 object location
L longitudinal direction
T transversal direction
V main radiation direction
A1 . . . A5 data samples
Z1 . . . Z6 data samples
S1 . . . S3 method steps

We claim:
1. Illumination device for photodynamic therapy,
the illumination device comprising five or more electromagnetic radiation emitting units,
each electromagnetic radiation emitting unit comprising several radiation sources,
the electromagnetic radiation sources being configured to generate radiation for the irradiation of a region of an irradiation object in an illumination session,
wherein the irradiation object is to be arranged at a predetermined object location,
wherein the predetermined object location is arranged at a distance relative to radiation output areas of the radiation emitting units through which the radiation generated by the electromagnetic radiation sources exits the respective radiation emitting unit during operation of the illumination device),
wherein in each radiation emitting unit
a plurality of radiation sources is arranged on a radiation source carrier,
the radiation sources on the radiation source carrier are grouped into a plurality of groups, wherein the radiation sources of each group are arranged in a regular, two-dimensional group pattern, wherein at least two groups of the plurality of groups have different group patterns,
each group comprises a plurality of radiation sources,
a first group with a first group pattern is arranged between a second and a third group, when seen in plan view of the radiation source,
the second and the third group have the same group pattern and the first group has a different group pattern,
the first group has a lower occupancy density with radiation sources than the second and third groups,
wherein the illumination device comprises a distance monitoring system, wherein the distance monitoring system is configured to monitor the distance of the irradiation object from the radiation emitting units, wherein the distance monitoring system comprises a plurality of distance sensors and each radiation emitting unit is assigned a distance sensor for measuring a distance between the irradiation object and the respective radiation emitting unit wherein the illumination device is configured such that each radiation emitting unit, is operable in a low-intensity mode when the distance of the radiation emitting unit to the irradiation object lies within an irradiation range of ±2.0 cm around a nominal distance of 12.0 cm or 12.5 cm, the low-intensity mode being a mode in which the radiation intensity emitted by the radiation emitting unit is at most 50% of a nominal radiation intensity used during the illumination session, wherein the nominal radiation intensity is the radiation intensity which results in the maximum irradiance of the irradiation object during the illumination session, is automatically switched from the low-intensity mode into a no-intensity mode when the distance of the radiation emitting unit to the irradiation object leaves the irradiation range, the no-intensity mode being a mode in which the radiation emitting unit does not emit radiation, is switchable from the low-intensity mode into a nominal-intensity mode, the nominal-intensity mode being a mode in which the radiation intensity is the nominal radiation intensity.

2. Illumination device according to claim 1, wherein an occupancy density of the radiation source carrier with radiation sources is smaller in a center region of the radiation source carrier than in peripheral regions of the radiation source carrier outside the center region.

3. Illumination device according to claim 2, wherein the electromagnetic radiation emitting units are configured to be arranged in a C-shape configuration and/or semi-circle configuration.

4. Illumination device according to claim 3, wherein the radiation source carrier is an elongate carrier with a main direction of extension defining a longitudinal direction (L).

5. Illumination device according to claim 3, wherein, when the distance of the radiation emitting units to the irradiation object is each the nominal distance, the illuminated area on the irradiation object illuminated by the radiation emitting units is at most 32 cm×26 cm and at least 26 cm×20 cm.

6. Illumination device according to claim 5, wherein, in each radiation emitting unit, the pattern of the radiation sources on the radiation source carrier is symmetrical relative to one axis or two axis, which are perpendicular.

7. Illumination device according to claim 6, wherein the occupancy density with radiation sources in the second and third group is at least 1.2 times and at most 5 times the occupancy density in the first group.

8. Illumination device according to claim 7, wherein the radiation emitting unit comprises a unit housing which defines an outer edge of the radiation emitting unit.

9. Illumination device according to claim 8, wherein, in at least one radiation emitting unit, an area on the radiation source carrier occupied with radiation sources is at most 28 cm×16 cm and at least 22 cm×10 cm.

10. Illumination device according to claim 9, wherein the radiation emitting unit comprises one continuous radiation source carrier common for all radiation sources of the radiation emitting unit.

11. Illumination device according to claim 10, wherein the radiation sources are optoelectronic components, wherein the emission spectrum of the optoelectronic components has a peak wavelength in the following range: 635 nm±5 nm.

12. Illumination device according to claim 11, wherein the radiation emitting units are movably connected to one another.

13. Illumination device according to claim 12, wherein in at least one radiation emitting unit, the distance sensor is located offset of a geometric center of the radiation source carrier when viewed in plan view.

14. Illumination device according to claim 13, wherein the distance monitoring system is configured to call for an adjustment of the operation of the illumination device by:

varying the distance between the respective radiation emitting unit and the irradiation object.

15. A method for treating a skin disease comprising the following steps:

a) applying a pharmaceutical substance to the surface of the skin in a region which is to be treated;

b) arranging the skin region to be treated in a predetermined object location of the illumination device according to claim 1, c) irradiating the skin region to be treated with the illumination device.

16. Method according to claim 15, comprising an execution of a start sequence prior to an illumination session, wherein the execution of the start sequence comprises:

switching on the radiation emitting units such that the respectively assigned distance sensor is activated for measuring the distance to the irradiation object, adjusting the distance of each radiation emitting unit to the irradiation object until the respective distance is within the irradiation range, when the distance of the respective radiation emitting unit is in the irradiation range, operating the radiation emitting units in the low-intensity mode in order to illuminate the irradiation object with a low radiation intensity, adjusting the position of the irradiation object relative to the illumination device while maintaining the distance of each radiation emitting unit to the irradiation object in the irradiation range, switching a radiation emitting unit from the low-intensity mode into the no-intensity mode if the distance of said radiation emitting unit to the irradiation object leaves the irradiation range, switching at least one radiation emitting unit into the nominal-intensity mode when the position of the irradiation object relative to the illumination device has been adjusted.

17. A method for operating an illumination device according to claim 1, comprising the steps of:

providing a measurement signal which is indicative for a distance between at least one radiation emitting unit and the radiation object, generating an operation signal as a function of the measurement signal, said operation signal being configured to trigger a call for an adjustment of the operation of the illumination device.

18. Computer program product comprising machine-readable instructions, which, when loaded and executed on a processor, are configured to cause the illumination device to execute the method of claim 17.

19. A computer-readable medium having stored thereon the computer program product according to claim 18.

20. Illumination device for photodynamic therapy, the illumination device comprising five or more electromagnetic radiation emitting units, each electromagnetic radiation emitting unit comprising several radiation sources, the electromagnetic radiation sources being configured to generate radiation for the irradiation of a region of an irradiation object in an illumination session, wherein the irradiation object is to be arranged at a predetermined object location, wherein the predetermined object location is arranged at a distance relative to radiation output areas of the radiation emitting units through which the radiation generated by the electromagnetic radiation sources exits the respective radiation emitting unit during operation of the illumination device, wherein the illumination device comprises a distance monitoring system, wherein the distance monitoring system is configured to monitor the location and/or the distance of the irradiation object from the radiation emitting units, wherein the distance monitoring system comprises a plurality of distance sensors and each radiation emitting unit is assigned a distance sensor for measuring a distance between the irradiation object and the respective radiation emitting unit, wherein the distance monitoring system is configured to call for an adjustment of the operation of the illumination device by varying the distance between the radiation emitting units and the irradiation object, wherein the illumination device is configured such that each radiation emitting unit, is operable in a low-intensity mode when the distance of the radiation emitting unit to the irradiation object lies within an irradiation range of ±2.0 cm around a nominal distance of 12.0 cm or 12.5 cm, the low-intensity mode being a mode in which the radiation intensity emitted by the radiation emitting unit is at most 50% of a nominal radiation intensity used during the illumination session, wherein the nominal radiation intensity is the radiation intensity which results in the maximum irradiance of the irradiation object during the illumination session, is automatically switched from the low-intensity mode into a no-intensity mode when the distance of the radiation emitting unit to the irradiation object leaves the irradiation range, the no-intensity mode being a mode in which the radiation emitting unit does not emit radiation, is switchable from the low-intensity mode into a nominal-intensity mode, the nominal-intensity mode being a mode in which the radiation intensity is the nominal radiation intensity, wherein in each radiation emitting unit a plurality of radiation sources is arranged on a radiation source carrier, the assigned distance sensor is located offset of a geometric center of the radiation source carrier when viewed in plan view.

\* \* \* \* \*